United States Patent [19]

Meyer et al.

[11] Patent Number: 5,521,181
[45] Date of Patent: May 28, 1996

[54] BICYCLIC SUBSTITUTED HEXAHYDROBENZ[E]ISOINDOLE α-1 ADRENERGIC ANTAGONISTS

[75] Inventors: Michael D. Meyer, Lake Villa; Robert J. Altenbach, Chicago; William A. Carroll, Evanston; Irene Drizin, Waukegan; Suzanne A. Lebold, Chicago; Edmund L. Lee, Lake Zurich; Kevin B. Sippy, Lindenhurst; Karin R. Tietje, Mundelein; Diane M. Yamamoto, Gurnee; James F. Kerwin, Jr., Grayslake, all of Ill.

[73] Assignee: Abbott Laboratories, Abbott Park, Ill.

[21] Appl. No.: 379,823

[22] Filed: Jan. 27, 1995

[51] Int. Cl.[6] .................. C07D 403/02; C07D 403/14; A61K 31/505; A61K 31/40
[52] U.S. Cl. .................. 514/249; 514/259; 514/265; 514/262; 514/258; 548/427; 544/255; 544/256; 544/257; 544/258; 544/262; 544/268; 544/276; 544/278; 544/279; 544/280; 544/284
[58] Field of Search .................. 544/278, 279, 544/280, 284, 255, 256, 257, 258, 262, 268, 276; 548/427; 514/258, 249, 259, 265, 262

[56] References Cited

U.S. PATENT DOCUMENTS 5,420,128  5/1995  Kiyokawa et al. .................. 514/246

*Primary Examiner*—Mukund J. Shah
*Assistant Examiner*—Matthew V. Grumbling
*Attorney, Agent, or Firm*—Jerry F. Janssen

[57] ABSTRACT

The present invention relates to a compound of the formula

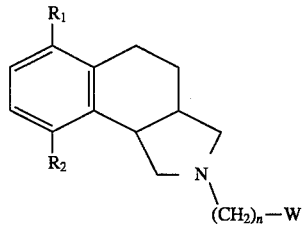

and the pharmaceutically acceptable salts thereof wherein W is a bicyclic heterocyclic ring system. The compounds are α-1 adrenergic antagonists and are useful in the treatment of BPH; also disclosed are α-1 antagonist compositions and a method for antagonizing α-1 receptors and treating BPH.

20 Claims, No Drawings

BICYCLIC SUBSTITUTED HEXAHYDROBENZ[E]ISOINDOLE α-1 ADRENERGIC ANTAGONISTS

TECHNICAL FIELD

The present invention relates to novel organic compounds and compositions which are alpha-1 (α-1) adrenoreceptor antagonism, processes for making such compounds, synthetic intermediates employed in these processes, and a method for inhibiting alpha-1 adrenoceptors and treating benign prostatic hyperplasia (BPH), also called benign prostatic hypertrophy.

BACKGROUND OF THE INVENTION

Adrenergic neurons play a major role in the innervation of heart, blood vessel and smooth muscle tissue. Compounds capable of interacting with adrenoceptor sites within adrenergic nerve can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within adrenergic neurons in order to obtain a desired physiological response separate from other possible, and perhaps less desirable, responses of the system.

Benign prostatic hyperplasia (BPH) is a condition which develops in middle-aged and elderly males and refers to the benign overgrowth of the stromal and epithelial elements of the prostate associated with aging. Symptoms of BPH include increased frequency of urination, nocturia, a weak urine stream and hesitancy or delay in starting the urine flow. Chronic consequences of BPH can include hypertrophy of bladder smooth muscle, a decompensated bladder and an increased incidence of urinary tract infection.

Typically, BPH begins at an age in the mid-fifties and is the most common cause of urinary tract problems of men of this age. BPH is apparently rare in men prior to age 40, but at age 60, approximately 50% of men have histological evidence of BPH. The prevalence of BPH continues to increase with age until, at age 80, approximately 80% of men have pathological evidence of BPH.

Although prostatic hyperplasia is a common finding in older men, the presence of urinary symptoms is the essential feature that distinguishes simple anatomic enlargement of the prostate from prostatism, which is the clinical syndrome whereby the patient experiences significant obstruction of urinary flow. It is not uncommon in older men to have a palpably enlarged prostate without showing the symptoms of prostatism. From the patient's perspective, however, the incidence and progression of urinary symptoms are more important than the mere presence of an enlarged prostate.

The discovery in the 1970's (M. Caine, et al., *Brit. J. Urol.*, 47: 193–202 (1975)) of large numbers of alpha-adrenergic receptors in the smooth muscle of the prostatic capsule and bladder neck led to the conclusion that there is both a static and a dynamic component to bladder outlet obstruction associated with BPH. The static component derives from the progressive hyperplasia of the prostate with aging, leading to urethral narrowing which causes symptoms of urinary obstruction. Superimposed on this essentially mechanical problem is the variable degree of smooth muscle contraction controlled by the sympatheic nervous system and which is affected by by factors such as stress, cold and sympathomimetic drugs. It is this dynamic component which explains the often rapid fluctuations in symptoms observed in patients with prostatism.

The currently most effective treatment for BPH is the surgical procedure of transurethral resection of the prostate (TURP) Since it removes the obstructing tissue (C. Chapple, *Br. Med. Journal* 304: 1198–1199 (1992)) it is a treatment which is directed to the static and dynamic components of BPH. However, this surgical treatment is associated with rates of mortality (1%) and adverse event (incontinence 2–4%, infection 5–10%, and impotence 5–10%). A non-invasive alternative treatment would thus be highly desirable.

The incidental clinical observation that urinary incontinence developed in women during antihypertensive treatment with prazosin (T. Thien, K. P. Delacre, F. M. J. Debruyne, R. A. P. Koene, *Br. Med. Journal*, 622–623 (1978)) and the experimental work of Caine (op cit.) contributed to the recognition of the potential role of selective α-1 adrenoceptor blockade in diseases of the lower urinary tract. Subsequent studies by several groups have documented the functional role of α-1 adrenoceptors relative to α-2 adrenoceptors in the stromal compartment of the prostate, thereby providing a putative molecular basis for the use of specific α-1 adrenoceptor blockers in the non-surgical management of BPH (C. R. Chapple, M. L. Aubry, S. James, M. Greengrass, G. Burnstock, R. T. Turner-Warwick, *Br. J. Urol.* 63: 487–496 (1989)). Clinical efficacy of α-1 antagonists in BPH has been demonstrated with several non-selective α-1 blockers, including terazosin (Hytrin™), prazosin, and doxazosin. Treatment periods as short as two to four weeks with α-1 adrenoceptor blockers have shown objective improvements in the mean and maximum urinary flow rates (14–96%) with subjective improvements in patients' symptom scores (R. A. Janknegt, C. R. Chapple, *Eur. Urol.* 24: 319–326 (1993)). Longer term studies with terazosin, indoramin, prazosin, and doxazosin have similarly demonstrated significant improvements in urinary flow rams and subjective symptom scores (R. A. Janknegt, op. cit., H. Lepor, G. Knapp-Maloney, *J. Urol.* 145: 263A (1991), W. Chow, D. Hahn, D. Sandhu, *Br. J. Urol.* 65: 36–38 (1990) and C. R. Chapple, T. J. Christmas, E. J. G. Milroy, *Urol. Int.* 45: 47–55 (1990)). However, these agents possess similar dose limiting side effects: hypotension, dizziness, and muscle fatigue. There thus exists a need for a "uroselective" α-1 antagonist with reduced side effect liabilities.

SUMMARY OF THE INVENTION

In its principle embodiment, the present invention provides certain hexahydro-[1H]-benz[e]isoindole compounds of the formula I:

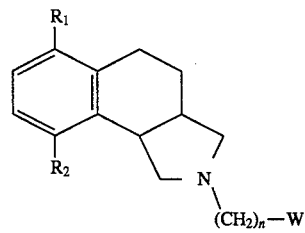

or a pharmaceutically acceptable salt thereof wherein n is an integer from 2 to 6.

$R_1$ and $R_2$ are independently selected from the group consisting of hydrogen, alkyl of one to six carbon atom, alkoxy of one to six carbon atoms, hydroxy, halo, carboxy, and alkoxycarbonyl of two to eight carbon atoms.

W is selected from the group consisting of

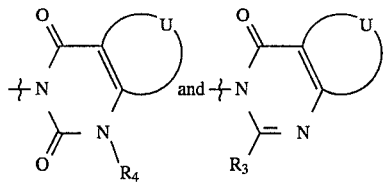

wherein $R_3$ is selected from the group consisting of hydrogen, alkyl of one to six carbon atoms, unsubstituted phenyl and phenyl substituted with alkyl of one to six carbon atoms, and $R_4$ is hydrogen or alkyl of one to six carbon atoms.

U, taken together with the carbon atoms to which it is attached forms a ring selected from the group consisting of (a) an unsubstituted or substituted five membered ring having four carbon atoms, two double bonds and one heteroatom selected from the group consisting of —N($R_5$)—, —O— and —S— wherein $R_5$ is hydrogen or alkyl of one to six carbon atoms and the ring substituent is selected from the group consisting of alkyl of one to six carbon atoms, phenyl, halo, cyano, nitro, carboxy, alkoxycarbonyl of two to eight carbon atoms and alkoxy of one to six carbon atoms; (b) an unsubstituted or substituted five membered ring having three carbon atoms, two double bonds and two heteroatoms selected from the group consisting of two nitrogen atoms, one oxygen atom and one nitrogen atom, and one sulfur atom and one nitrogen atom wherein the ring substituent is selected from the group consisting of alkyl of one to six carbon atoms, phenyl, halo, cyano, nitro, carboxy, alkoxycarbonyl of two to eight carbon atoms and alkoxy of one to six carbon atoms; (c) a benzene ring which is unsubstituted or substituted with a substituent selected from the group consisting of alkyl of one to six carbon atoms, phenyl, halo, cyano, nitro, carboxy, alkoxycarbonyl of two to eight carbon atoms and alkoxy of one to six carbon atoms methylenedioxy and ethylenedioxy; and (d) an unsubstituted or substituted six membered ring having one to three double bonds and one or two nitrogen atoms, wherein the ring substituent is selected from the group consisting of alkyl of one to six carbon atoms, phenyl, halo, cyano, nitro, carboxy, alkoxycarbonyl of two to eight carbon atoms and alkoxy of one to six carbon atoms In one embodiment, the present invention provides a compound of the formula

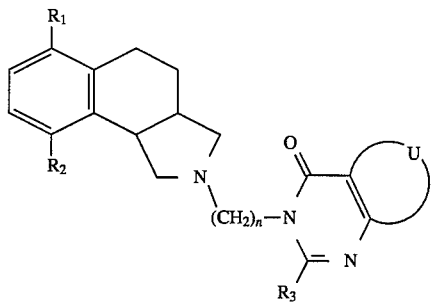

(II)

wherein $R_1$, $R_2$, n, $R_3$ and U are as previously defined.

In another embodiment, the present invention provides a compound of the formula

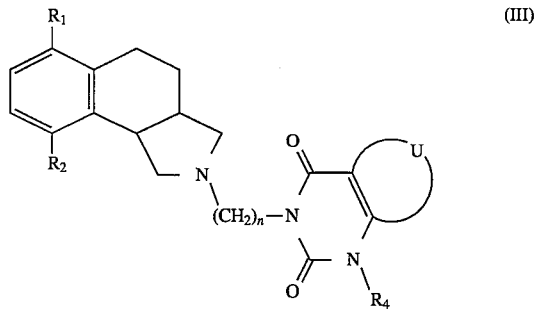

(III)

wherein $R_1$, $R_2$, n, $R_4$ and U are as previously defined.

Yet another embodiment of the present invention provides a compound of formula (I) wherein W is selected from the group consisting of

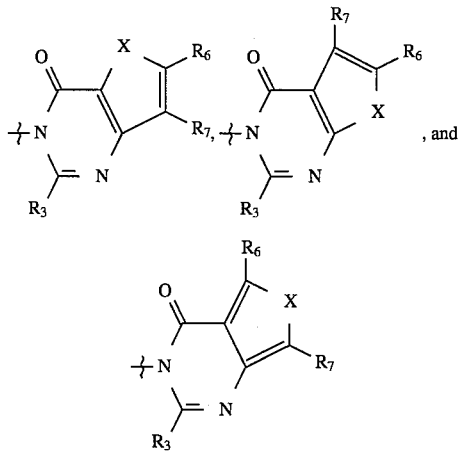

wherein X is selected from the group consisting of —N($R_5$)—, —O— and —S— wherein $R_5$ is hydrogen or alkyl of one to six carbon atoms, $R_6$ and $R_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and $R_3$ is as previously defined.

In yet another embodiment of the present invention provides a compound of formula (I) wherein W is selected from the group consisting of

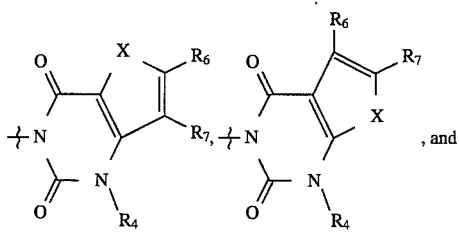

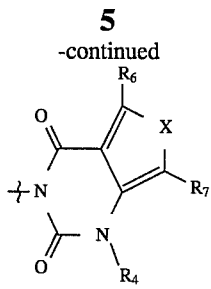

wherein X is selected from the group consisting of —N(R$_5$)—, —O— and —S— wherein R$_5$ is hydrogen or alkyl of one to six carbon atoms, R$_6$ and R$_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and R$_4$ is as previously defined.

Another embodiment of the present invention provides a compound of formula (I) wherein W is selected from the group consisting of

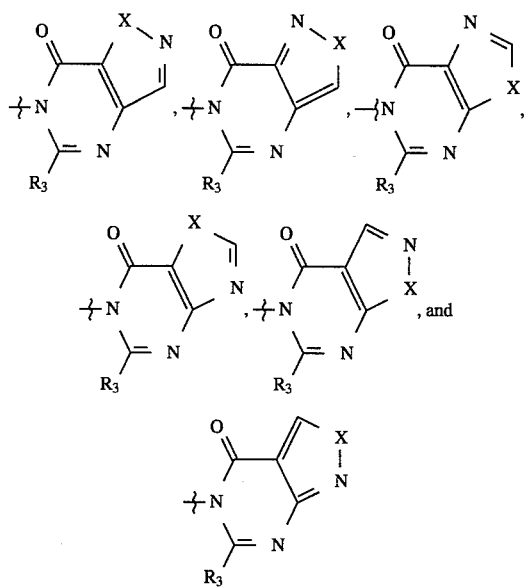

wherein X is selected from the group consisting of —N(R$_5$)—, —O— and —S— wherein R$_5$ is hydrogen or alkyl of one to six carbon atoms and R$_3$ is as previously defined.

Another embodiment of the present invention provides a compound of formula (I) wherein W is selected from the group consisting of

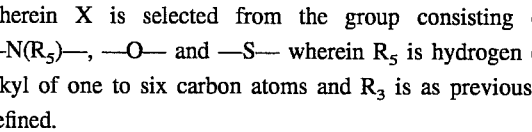
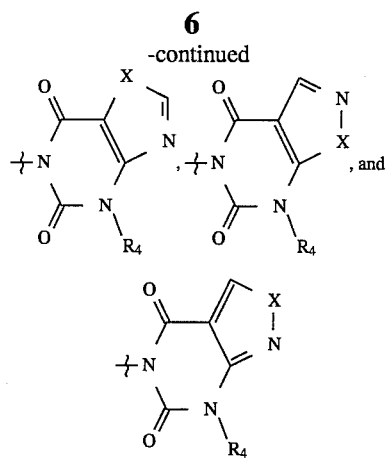

wherein X is selected from the group consisting of —N(R$_5$)—, —O— and —S— wherein R$_5$ is hydrogen or alkyl of one to six carbon atoms and R$_4$ is as previously defined.

Yet another embodiment of the present invention provides a compound of formula (I) wherein W is

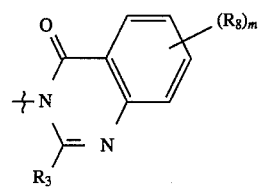

wherein m is selected from 1, 2 and 3 and, when m is 2 or 3, R$_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is 2, methylenedioxy and ethylenedioxy, and R$_3$ is as previously defined.

Another embodiment of the present invention provides a compound of formula (I) wherein W is

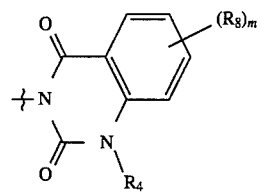

wherein m is selected from 1, 2 and 3 and, when m is 2 or 3, R$_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is 2, methylenedioxy and ethylenedioxy, and R$_4$ is as previously defined.

In yet another embodiment, the present invention provides a compound of formula (I) wherein W is selected from the group consisting of

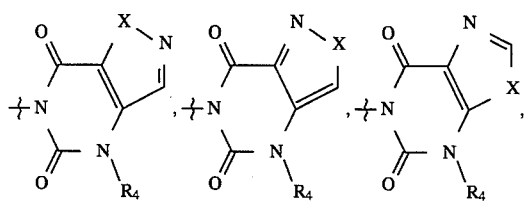

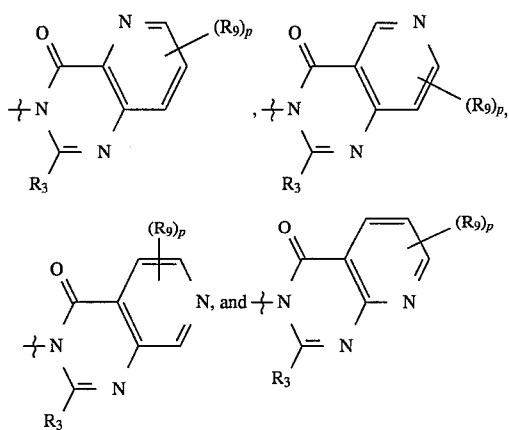

wherein p is selected from 1 and 2 and, when p is 2, $R_9$ at each occurence is independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and $R_3$ is as previously defined.

Another embodiment of the present invention provides a compound of formula (I) wherein W is selected from the group consisting of

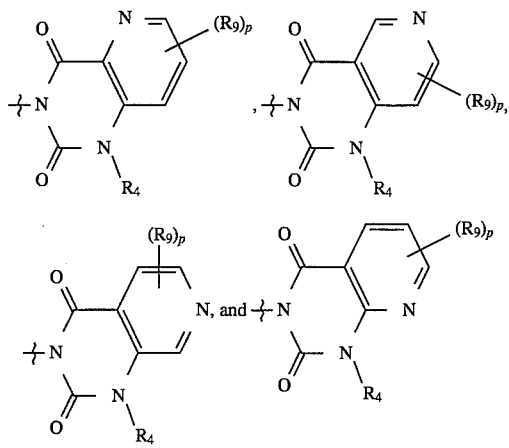

wherein p is selected from 1 and 2 and, when p is 2, $R_9$ at each occurence is independently selected from the group consisting of hydrogen, alkyl of one to six carbon atoms, phenyl, halo, cyano, nitro, carboxy, alkoxycarbonyl of two to eight carbon atoms, and alkoxy of one to six carbon atoms, and $R_4$ is as previously defined.

Another embodiment of the present invention provides a compound of formula (I) wherein W is selected from the group consisting of

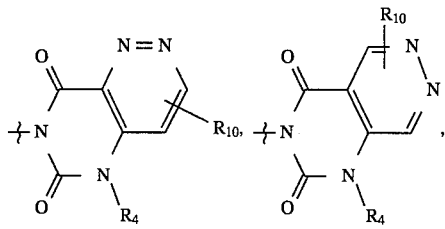

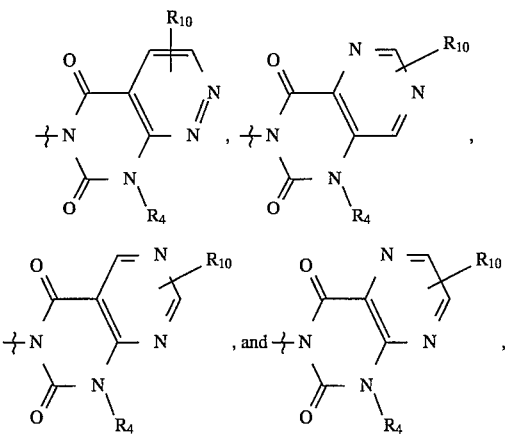

wherein $R_{10}$ is selected from the group consisting of hydrogen, alkyl of one to six carbon atoms, phenyl, halo, cyano, nitro, carboxy, alkoxycarbonyl of two to eight carbon atoms and alkoxy of one to six carbon atoms and $R_4$ is as previously defined.

Another embodiment of the present invention provides a compound of formula (I) wherein W is selected from the group consisting of

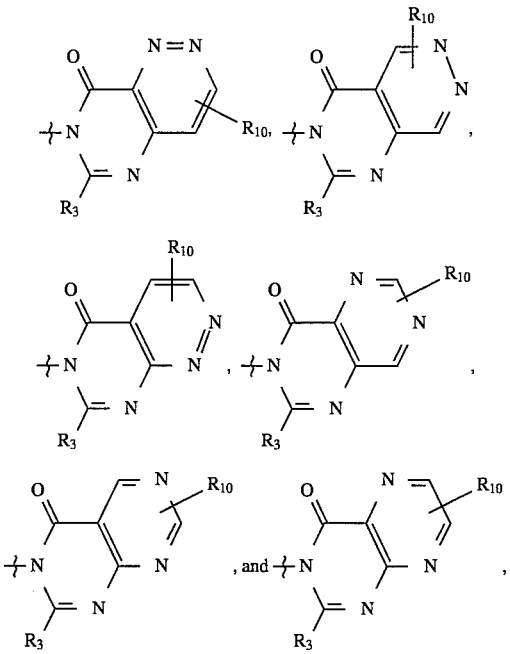

wherein $R_{10}$ is selected from the group consisting of hydrogen, alkyl of one to six carbon atoms, phenyl, halo, cyano, nitro, carboxy, alkoxycarbonyl of two to eight carbon atoms, and alkoxy of one to six carbon atoms and $R_3$ is as previously defined.

A preferred embodiment of the present invention provides a compound of formula (I) wherein W is selected from the group consisting of

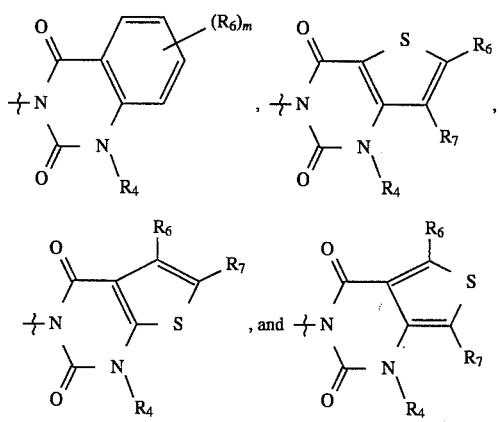

wherein $R_1$, $R_2$, n, m, $R_4$, $R_6$, $R_7$ and $R_8$ are as previously defined.

A more preferred embodiment of the present invention is a compound of formula (I) wherein one of $R_1$ and $R_2$ is alkoxy of one to six carbon atoms and the other one is hydrogen, n is selected from an integer from 2 to 4 and W is selected from the group consisting of

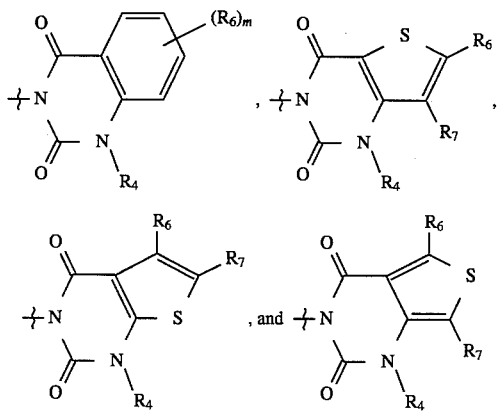

wherein $R_1$, $R_2$, n, m, $R_4$, $R_6$, $R_7$ and $R_8$ am as previously defined.

The present invention also relates to pharmaceutical compositions which comprise a therapeutically effective amount of a compound of claim 1 in combination with a pharmaceutically acceptable carrier.

The invention further relates to a method of antagonizing α-1 receptors in a host mammal in need of such treatment a therapeutically effective amount of a compound of claim 1.

The invention still further relates to a method of treating BPH in a host mammal in need of such treatment a therapeutically effective amount of a compound of claim 1.

DETAILED DESCRIPTION OF THE INVENTION

As used throughout this specification and the appended claims, the following terms have the meaning specified.

The term "alkyl" as used herein refer to straight or branched chain alkyl radicals including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to an alkyl group, as previously defined, attached to the parent molecular moiety through an oxygen atom. Examples of alkoxy include, but are not limited to, methoxy, ethoxy, isopropoxy, tert-butoxy, and the like.

The term "alkoxycarbonyl" as used herein refers to an alkoxyl group as previously defined appended to the parent molecular moiety through a carbonyl group. Examples of alkoxycarbonyl include, but are not limited to, methoxycarbonyl, ethoxycarbonyl, isopropoxycarbonyl and the like.

The term "ethylenedioxy" as used herein refers to —O—CH$_2$—CH$_2$—O— which when attached to two adjacent positions on a benzene ring forms a six-membered ring.

The term "methylenedioxy" as used herein refers to —O—CH$_2$—O— which when attached to two adjacent positions on a benzene ring forms a 5-membered ring.

By "pharmaceutically acceptable salt" is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharm. Sciences*, 66: 1–19 (1977). The compounds of the present invention can be used in the form of salts derived from inorganic or organic acids. The salts can be prepared in situ during the final isolation and purification of the compounds of the invention, or separately by reacting the free base function with a suitable organic acid. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Asymmetric centers may exist in the compounds of the present invention. The present invention comtemplates the various stereoisomers and mixtures thereof. Starting compounds of particular stereochemistry are either commercially available or are made by the methods detailed below and resolved by techniques well known in the art of organic chemistry.

Representative examples of compounds falling within the scope of this invention include:

3-[2-(cis-9-methoxy-2,3,3a,4,5,9b-hexahydro-[1H]-benz[e]isoindol-1-yl)ethyl] -[1H,3H]-quinazoline-2,4(1H,3H)-dione;

3-[2-(cis-9-methoxy-2,3,3a,4,5,9b-hexahydro-[1H]-benz[e]isoindol-1-yl)ethyl]-7-methylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5-methylthieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5-phenyl-thieno[2,3-d]pyrimidine-2,4(1H,3H)-dione hydrochloride;

3-[2-(cis-6-methoxy-2,3,3a,4,5,9b-hexahydro-[1H]-benz[e]isoindol-1-yl)ethyl]-6-phenyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-thieno[3,4-d]pyrimidine-2,4(1H,3H)-dione;

3-[2-(cis-6-methoxy-2,3,3a,4,5,9b-hexahydro-[1H]-benz[e]isoindol-1-yl)ethyl]-8-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7-chloro-quinazoline-2,4(1H,3H)-dione;

3-[2-(cis-6-methoxy-2,3,3a,4,5,9b-hexahydro-[1H]-benz[e]isoindol-1-yl)ethyl]-5-methyl-quinazoline-2,4(1H,3H)-dione;

3-[2-((3aR,9bR)-cis-6-methoxy -2,3,3a,4,5,9b-hexahydro-[1H]-benz[e]isoindol-1-yl)ethyl]-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(cis-6-methoxy-2,3,3a,4,5,9b-hexahydro-[1H]-benz[e]isoindol-1-yl)ethyl]-6-fluoro-quinazoline-2,4(1H,3H)-dione;

3-[2-(cis-6-methoxy-2,3,3a,4,5,9b-hexahydro-[1H]-benz[e]isoindol-1-yl)ethyl]-6-nitro-quinazoline-2,4(1H,3H)-dione;

3-[2-(cis-6-methoxy-2,3,3a,4,5,9b-hexahydro-[1H]-benz[e]isoindol-1-yl)ethyl]-6-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7,8-trimethoxy-quinazoline-2,4(1H,3H)-dione;

3-[2-(cis-6-methoxy-2,3,3a,4,5,9b-hexahydro-[1H]-benz[e]isoindol-1-yl)ethyl]-8-methyl-quinazoline-2,4(1H,3H)-dione;

3-[2-(cis-6-methoxy-2,3,3a,4,5,9b-hexahydro-[1H]-benz[e]isoindol-1-yl)ethyl]-6,8-dimethyl-quinazoline-2,4(1H,3H)-dione;

3-[2-(cis-6-methoxy-2,3,3a,4,5,9b-hexahydro-[1H]-benz[e]isoindol-1-yl)ethyl]-pyrido[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5-chloro-quinazoline-2,4(1H,3H)-dione;

3-[2-(cis-6-methoxy-2,3,3a,4,5,9b-hexahydro-[1H]-benz[e]isoindol-1-yl)ethyl]-pyrido[3,4-d]pyrimidine-2,4(1H,3H)-dione;

3-[2-(cis-6-methoxy-2,3,3a,4,5,9b-hexahydro-[1H]-benz[e]isoindol-1-yl)ethyl]-7-fluoro-quinazoline-2,4(1H,3H)-dione;

3-[2-(cis-6-methoxy-2,3,3a,4,5,9b-hexahydro-[1H]-benz[e]isoindol-1-yl)ethyl]-1-methyl-quinazoline-2,4(1H,3H)-dione;

3-[2-(cis-6-methoxy-2,3,3a,4,5,9b-hexahydro-[1H]-benz[e]isoindol-1-yl)ethyl]-pyrido[4,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-1H-pyrazolo[3,4-d]pyrimidine-4,6(5H,7H)-dione;

3-[2-(cis-6-methoxy-2,3,3a,4,5,9b-hexahydro-[1H]-benz[e]isoindol-1-yl)ethyl]-6-methylthieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1H-pyrrolo[2,3-d]pyrimidine-2,4(3H,7H)-dione;

3-[2-(cis-6-methoxy-2,3,3a,4,5,9b-hexahydro-[1H]-benz[e]isoindol-1-yl)ethyl]-7-phenylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-6-phenylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-4(3H)-one;

3-[2-(cis-6-methoxy-2,3,3a,4,5,9b-hexahydro-[1H]-benz[e]isoindol-1-yl)ethyl]-quinazoline-4(3H)-one;

3-[2-(cis-6-hydroxy-2,3,3a,4,5,9b-hexahydro-[1H]-benz[e]isoindol-1-yl)ethyl]-thieno[2,3-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-quinazoline-2(1H)-one;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-ethylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-1-methyl-6,7-dimethoxyquinazoline-2,4(1H,3H)-dione;

3-[2-(cis-6-methoxy-2,3,3a,4,5,9b-hexahydro-[1H]-benz[e]isoindol-1-yl)ethyl]-6-methoxy-thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxy-quinazoline-4(3H)-one;

3-[2-((3aR,9bR)-cis-6-methoxy-2,3,3a,4,5,9b-hexahydro-[1H]-benz[e]isoindol-1-yl)ethyl]-thieno[2,3-d]pyrimidine-4(3H)-one;

3-[2-((3aR,9bR)-cis-6-methoxy-2,3,3a,4,5,9b-hexahydro-[1H]-benz[e]isoindol-1-yl)ethyl]-quinazoline-2(1H)-one;

3-[2-(cis-6-methoxy-2,3,3a,4,5,9b-hexahydro-[1H]-benz[e]isoindol-1-yl)ethyl]-quinazoline-4(3H)-one;

2-[2-(cis-6-methoxy-2,3,3a,4,5,9b-hexahydro-[1H]-benz[e]isoindol-1-yl)ethyl]-1,2,3,4-tetrahydroisoquinolin-1,3-dione;

2-[2-(cis-6-methoxy-2,3,3a,4,5,9b-hexahydro-[1H]-benz[e]isoindol-1-yl)ethyl]-6,7-dimethoxy-1,2,3,4-tetrahydroisoquinoline;

3-[2-(cis-6-methoxy-2,3,3a,4,5,9b-hexahydro-[1H]-benz[e]isoindol-1-yl)ethyl]-2,4-pteridinedione;

3-[2-(cis-6-methoxy-2,3,3a,4,5,9b-hexahydro-[1H]-benz[e]isoindol-1-yl)ethyl]-7-(3,4-dimethoxyphenyl)-thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-6-chlorothieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-6-dimethylaminocarbonyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]oxazolo[5,4-d]pyrimidine-5,7(4H,6H)-dione;

3-[2-(cis-6-methoxy-2,3,3a,4,5,9b-hexahydro-[1H]-benz[e]isoindol-1-yl)ethyl]-7-amino-oxazolo[5,4-d]pyrimidin-5(6H)-one;

1-[2-(cis-6-methoxy-2,3,3a,4,5,9b-hexahydro-[1H]-benz[e]isoindol-1-yl)ethyl]-3,9-dimethyl-[1H]-purine-2,6-dione;

1-[2-(cis-6-methoxy-2,3,3a,4,5,9b-hexahydro-[1H]-benz[e]isoindol-1-yl)ethyl]-3,7-dimethyl-[7H]-imidazo[4,5-d]pyrimidin-2,6-dione;

3-[4-(cis-9-methoxy-2,3,3a,4,5,9b-hexahydro-[1H]-benz[e]isoindol-1-yl)butyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7,8-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7-methoxy-quinazoline-2,4(1H,3H)-dione;

3-[2-(cis-6-methoxy-2,3,3a,4,5,9b-hexahydro-[1H]-benz[e]isoindol-1-yl)ethyl]-7,8-dimethyl-quinazoline-2,4(1H,3H)-dione;

3-[2-(cis-6-methoxy-2,3,3a,4,5,9b-hexahydro-[1H]-benz[e]isoindol-1-yl)ethyl]-7-methylsulfonylamino-quinazoline-2,4(1H,3H)-dione;

3-[2-(cis-6-methoxy-2,3,3a,4,5,9b-hexahydro-[1H]-benz[e]isoindol-1-yl)ethyl]-7,8-ethylenedioxy-quinazoline-2,4(1H,3H)-dione;

3-[2-(cis-6-hydroxy-2,3,3a,4,5,9b-hexahydro-[1H]-benz[e]isoindol-1-yl)ethyl]-6,7-dimethoxy-quinazoline-2,4(1H,3H)-dione;

2-[2-(cis-6-methoxy-2,3,3a,4,5,9b-hexahydro-[1H]-benz[e]isoindol-1-yl)ethyl]-4-amino-6,7-dimethoxy-quinazoline;

3-[2-(cis-6-methoxy-2,3,3a,4,5,9b-hexahydro-[1H]-benz[e]isoindol-1-yl)ethyl]-6-chloro-7-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6-methoxy-7-chloro-quinazoline-2,4(1H,3H)-dione;

3-[2-(cis-6-methoxy-2,3,3a,4,5,9b-hexahydro-[1H]-benz[e]isoindol-1-yl)ethyl]-7-dimethylaminocarbonyl-quinazoline-2,4(1H,3H)-dione;

3-[2-(cis-6-methoxy-2,3,3a,4,5,9b-hexahydro-[1H]-benz[e]isoindol-1-yl)ethyl]-7-cyano-quinazoline-2,4(1H,3H)-dione;

3-[2-(trans-9-methoxy-2,3,3a,4,5,9b-hexahydro-[1H]-benz-[e]isoindol-1-yl)ethyl]-[1H,3H]-quinazoline-2,4(1H,3H)-dione;

3-[2-(trans-6-methoxy-2,3,3a,4,5,9b-hexahydro-[1H]-benz[e]isoindol-1-yl)ethyl]-thieno[3,2-d]pyrimidine-2,4(1H,3H)-dione;

3-[2-(trans-6-methoxy-2,3,3a,4,5,9b-hexahydro-[1H]-benz[e]isoindol-1-yl)ethyl]-8-methoxy-quinazoline-2,4(1H,3H)-dione;

3-[2-(trans-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(trans-6-methoxy-2,3,3a,4,5,9b-hexahydro-[1H]-benz[e]isoindol-1yl)ethyl]-7-chloro-quinazoline-2,4(1H,3H)-dione;

3-[2-(trans-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(trans-6-methoxy-2,3,3a,4,5,9b-hexahydro-[1H]-benz[e]isoindol-1-yl)ethyl]-6,7,8-trimethoxy-quinazoline-2,4(1H,3H)-dione;

3-[2-(trans-6-methoxy-2,3,3a,4,5,9b-hexahydro-[1H]-benz[e]isoindol-1-yl)ethyl]-1-methylquinazoline-2,4(1H,3H)-dione;

3-[2-(trans-6-methoxy-2,3,3a,4,5,9b-hexahydro-[1H]-benz[e]isoindol-1-yl)ethyl]-6,7-dimethoxy-quinazoline-4(3H)-one;

3-[2-(trans-6-methoxy-2,3,3a,4,5,9b-hexahydro-[1H]-benz[e]isoindol-1yl)ethyl]-6,7-methylenedioxyquinazoline-2,4(1H,3H)-dione;

3-[2-(trans-6-methoxy-2,3,3a,4,5,9b-hexahydro-[1H]-benz[e]isoindol-1-yl)ethyl]-6,7-ethylenedioxyquinazoline-2,4(1H,3H)-dione;

3-[2-(trans-6-methoxy-2,3,3a,4,5,9b-hexahydro-[1H]-benz[e]isoindol-1-yl)ethyl]-1-methyl-6,7-dimethoxyquinazoline-2,4(1H,3H)-dione; and 3-[2-(trans-6-methoxy-2,3,3a,4,5,9b-hexahydro-[1H]-benz[e]isoindol-1-yl)ethyl]-6-methoxy-thieno[3,2-d]pyrimidine-2,4(1H,3H)-dione; or a pharmaceutically acceptable salt thereof.

Preferred compounds are selected from those having formula (I) wherein one of $R_1$ and $R_2$ is alkoxy of one to six carbon atoms and the other one is hydrogen, n is selected from an integer from 2 to 4, and W is selected from the group consisting of

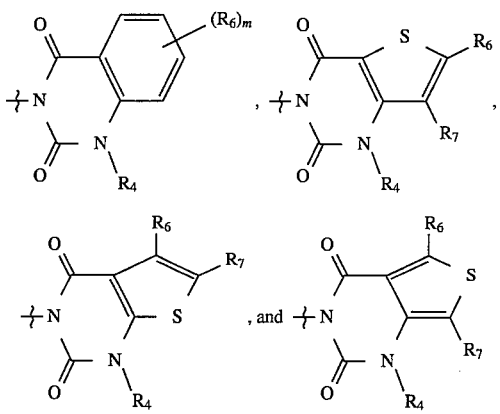

wherein m is selected from 1, 2 and 3, $R_6$ and $R_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, $R_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is two, methylenedioxy and ethylenedioxy, and $R_4$ is as previously defined is selected from the group consisting of:

3-[2-(cis-6-methoxy-2,3,3a,4,5,9b-hexahydro-[1H]-benz[e]isoindol-1-yl)ethyl]-8-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7-chloro-quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(cis-6-methoxy-2,3,3a,4,5,9b-hexahydro-[1H]-benz[e]isoindol-1-yl)ethyl]-6-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,8-dimethyl-quinazoline-2,4(1H,3H)-dione;

3-[2-(cis-6-methoxy-2,3,3a,4,5,9b-hexahydro-[1H]-benz[e]isoindol-1-yl)ethyl]-1-methyl-quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)-cis-6-methoxy-2,3 3a,4,5,9b-hexahydro-[1H]-benz[e]isoindol-1-yl)ethyl]-6,7-ethylenedioxyquinazoline-2,4(1H,3H)-dione;

3-[2-((3aR,9bR)-cis-6-methoxy-2,3,3a,4,5,9b-hexahydro-[1H]-benz[e]isoindol- 1-yl)ethyl]-6,7-dimethoxyquinazoline-2,4(1H,3H)-dione; and 3-[2-((3aR,9bR)-cis-6-methoxy-23,3a,4,5,9b-hexahydro-[1H]-benz[e]isoindol- 1-yl)ethyl]-6,7-dimethoxy-quinazoline-4(H)-one;

or a pharmaceutically acceptable salt thereof.

As an indication that the compounds described herein act through binding to α-1 receptors, the compounds have been evaluated for their ability to displace prazosin from its receptor.

IN VITRO BINDING ASSAYS

In the following, for purposes of discussing alpha-1 receptor subtypes, the IUPAC convention of using lower case letters to define molecular clones and upper case letters to indicate pharmacologically defined receptors has been followed. Moreover, the newly recommended nomenclature for alpha-1 ($\alpha_{1a}$, $\alpha_{1b}$, $\alpha_{1d}$) has been used.

Representative compounds of the invention were evaluated for α-adrenoceptor binding affinity in vitro using [$^3$H]-prazosin as the radioligand and three cloned α-1 adrenoceptors expressed in LTK cells: α-1: α-1a (bovine), α-1b (hamster) and α-1d (rat). Additionally, binding affinity against the pharmacologically defined α-1A adrenoceptor (rat submaxillary gland) was measured.

The cDNA clones encoding the α-1 receptors (α-1a, α-1b, and α-1d) were obtained from TULCO (Triangle Universities Licensing Consortium, Research Triangle Park, N.C.) and inserted into the eukaryotic expression vector SnaB30. In this vector, expression of the receptor gene is under the transcriptional control of an SV40 early promoter. Positive drug selection is provided by a neomycin-resistance gene. Mouse fibroblast cells (LTK) were transfected with the $\alpha_1$ expression plasmids and grown in Dulbecco's modified Eagle's medium (DMEM) containing 10% fetal calf serum and 30 μM G418. Stable G418-resistant parental lines were generated, with successful expression of receptor protein monitored using radioligand binding techniques. Stable single cell clones derived from the parental lines were screened in receptor binding assays to identify clones having high receptor density. Roller bottle cultures of the cloned lines were used to provide cell membranes for subsequent receptor binding characterization studies. A cell line containing the SnaB30 vector expressing the human erythropoietin gene served as a negative control.

For receptor binding assays, large scale membrane preparations were utilized in which 6 million cells were seeded into small (450 cm$^2$) Corning tissue culture roller bottles. 200 mL of DMEM containing 10% fetal calf serum and 300 μM G418 were added to each roller bottle. A 95% air/5% CO$_2$ gas mixture (sterile) was injected into each roller bottle prior to sealing. The bottles were then incubated at 37° C. on a roller rack for 5 days. Cells were re-fed with fresh medium after 3 days in culture.

On the fifth day of culture, growth medium was removed from cells grown in roller bottles, and the cells were washed twice with PBS (Sigma, 120 mM NaCl, 2.7 mM KCl, 10 mM Na$_2$HPO$_4$-NaH$_2$PO$_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000 ×G for 5 min at 2°–4° C., washed with PBS and recentrifuged. The supernatant was decanted and the pellet weighed to determine the wet weight of cells. Cells were washed a final time in 40 vol 5 mM Tris-HCl, 5 mM EDTA, pH=7.7, and centrifuged at 40,000×G for 10 minutes. Cells were homogenized in 10 mL of 50 mM Tris-HCl, 5 mM EDTA (pH=7.4) and diluted to 40 mL/tube. Homogenates were centrifuged at 40,000×G for 10 minutes. The supernatant was decanted and the pellets rehomogenized in 50 mM Tris-HCl (pH=7.4) and centrifuged as before. The supernatant was decanted and the homogenate resuspended in 6.25 volumes (per gram wet weight of 50 mM Tris-HCl and aliquots of the pooled homogenates s frozen in liquid N$_2$ and stored at −70° C. until the time of assay. Rat submaxillary glands were used for α-1A receptors and were prepared essentially as described (Michel, A. D., Loury, D. N. and Whiting, R. L., *Brit. J. Pharmacol.* 98: 83–889 (1989)).

Receptor binding assays for α-1 receptors were performed essentially as described by Greengrass and Bremner (*Eur. J. Pharmacol.* 55: 323–326 (1979)). Briefly, plastic Bioblocks™ (DBM Scientific, Valencia, Calif.) were incubated at 25° C. for 50 minutes with 500 µL of membrane homogenate (diluted with an additional 96 volumes [for cloned receptors, 12 volumes for submaxillary gland] in 50 mM Tris-HCl buffer (pH=7.7 at the time of assay), 450 µL of [$^3$H]prazosin (0.2 nM final concentration, 75–85 Ci/mmole, DuPont-NEN Corp., Boston, Mass.) and 50 µL of either water (for total binding) or 10 µM phentolamine (final concentration, for non-specific binding). Following equilibration, bound radioligand was separated from free on GF/B filters (presoaked in 0.5% polyethyleneimine) using either a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., *J. Receptor Res.* 8: 23–46 (1988)).

Canine prostate strips were used in vitro as previously described (Hieble, J. P., Boyce, A. J. and Caine, M., *Fed. Proc.*, 45: 2609–2614 (1986)), to determine antagonist potencies against phenylephrine-induced contractions.

The results are shown in Table I. The results show that the compounds of the invention bind to the α-1 adrenoceptor and show varying degrees of specificity for the α-1a receptor.

TABLE 1

In Vitro Data for Binding to α-1 Adrenoceptors

| Ex. No. | α-1A (Rat) (nM) | α-1b (Hamster) (nM) | α-1a (Bovine) (nM) | α-1d (Rat) (nM) |
|---|---|---|---|---|
| 1 | 1.012 | 1.84 | 0.212 | 0.893 |
| 2 | 0.847 | 1.28 | 0.182 | 0.707 |
| 3 | 2.468 | 3.65 | 0.443 | 2.381 |
| 4 | 3.704 | 3.803 | 1.489 | 2.681 |
| 5 | 1.392 | 1.631 | 0.268 | 0.919 |
| 6 | 16.588 | 11.806 | 2.149 | 15.92 |
| 7 | 14.912 | 14.186 | 2.812 | 55.718 |
| 8 | 0.481 | 1.015 | 0.203 | 0.517 |
| 9 | 0.845 | 2.273 | 0.19 | 1.155 |
| 10 | 0.666 | 10.601 | 0.149 | 3.384 |
| 11 | 0.57 | 2.708 | 0.042 | 0.584 |
| 12 | 1.891 | 1.038 | 0.501 | 1.132 |
| 13 | 0.971 | 1.982 | 0.254 | 0.97 |
| 14 | 0.318 | 1.936 | 0.086 | 2.051 |
| 15 | 1.341 | 2.48 | 0.239 | 1.96 |
| 16 | 8.027 | 15.407 | 1.225 | 2.715 |
| 17 | 1.377 | 4.952 | 0.318 | 1.12 |
| 18 | 1.704 | 17.385 | 0.579 | 5.66 |
| 19 | 0.371 | 1.4 | 0.048 | 0.814 |
| 20 | 2.731 | 16.279 | 0.425 | 2.863 |
| 21 | 1.19 | 3.31 | 0.472 | 1.995 |
| 22 | 2.732 | 6.471 | 0.939 | 2.153 |
| 23 | 0.604 | 1.017 | 0.052 | 0.711 |
| 24 | 1.414 | 3.103 | 0.311 | 1.783 |
| 25 | 0.931 | 1.622 | 0.199 | 0.952 |
| 26 | 0.407 | 1.326 | 0.089 | 1.333 |
| 27 | 4.435 | 10.576 | | 2.872 |
| 28 | 43.665 | 66.695 | 10.098 | 42.764 |
| 29 | 3.437 | 9.292 | 0.978 | 2.88 |
| 30 | 1.205 | 2.587 | 0.483 | 1.671 |
| 31 | 0.302 | 0.426 | 0.124 | 0.599 |
| 32 | 7.773 | 11.349 | 0.139 | 4.403 |
| 33 | 1.349 | 24.279 | | 16.595 |
| 34 | 1.275 | 4.285 | | 2.839 |
| 35 | 47.195 | 97.372 | | 36.631 |

TABLE 1-continued

In Vitro Data for Binding to α-1 Adrenoceptors

| Ex. No. | α-1A (Rat) (nM) | α-1b (Hamster) (nM) | α-1a (Bovine) (nM) | α-1d (Rat) (nM) |
|---|---|---|---|---|
| 36 | 7.576 | 11.165 | | 3.378 |
| 37 | 0.021 | 0.567 | | 0.159 |
| 38 | 0.097 | 0.341 | | 0.105 |
| 39 | 0.28 | 6.33 | | 1.401 |
| 42 | 0.277 | 16.007 | | 7.048 |
| 44 | 7.576 | 11.165 | | 3.378 |

FUNCTIONAL ANTAGONISM AT α1 ADRENOCEPTORS

Functional assays indicative of pharmacologically defined α-1 adrenoceptors were used to further characterize compounds. Inhibition of phenylephrine (PE)-induced contraction of canine prostate smooth muscle can be correlated with α-1A adrenoceptor activation. Inhibition of PE-induced contraction of rat spleen is representative of α-1B adrenoceptor antagonism and inhibition of PE-induced contraction of rat was deferens correlates with α-1A adrenoceptor antagonism (R. P. Burt, C. R. Chapple and I. Marshall, *Br. J. Pharmacol.* 107: P324 (1992)). For each of these models, agonist dose response curves were repeated against increasing concentrations of test agent to derive a Schild plot [log (EC$_{50}$–1) against log (molarity of test agent)] to determine the pA$_2$. Data for prazosin, terazosin and doxazosin actually demonstrate a more potent effect on spleen smooth muscle by approximately an order of magnitude.

Canine prostate strips were used in vitro as previously described (Hieble, J. P., Boyce, A. J. and Caine, M., *Fed. Proc.*, 45: 2609–2614 (1986)), to determine antagonist potencies against phenylephrine-induced contractions.

The results are shown in Tables 2a and 2b. The results show that the compounds of the invention exhibit functional antagonism of α-1 adrenoceptors.

TABLE 2a

In Vitro Data for Functional Antagonism α-1 Adrenoceptors

| Ex. No. | pA$_2$ Rat Vas Deferens [α-1A] | pA$_2$ Rat Spleen [α-1B] | pA$_2$ Dog Prostate [α-1A] |
|---|---|---|---|
| 1 | 8.49 | 8 | 9.29 |
| 2 | 8.4 | 8.16 | 9.16 |
| 3 | 8.33 | 7.91 | 8.68 |
| 5 | 8.19 | 8.36 | 9.16 |
| 8 | 8.52 | 8.26 | 9.34 |
| 9 | 8.62 | 8.05 | 9.39 |
| 10 | 8.04 | 6.89 | 8.97 |
| 11 | 8.69 | | 8.92 |
| 12 | 8.07 | 8.17 | 7.67 |
| 13 | 8.12 | 8.37 | 9.07 |
| 33 | 8.95 | 7.69 | 8.87 |
| 39 | 8.53 | 7.52 | |
| 42 | 8.24 | 7.4 | 9.58 |
| prazosin | 8.78 | 9.51 | 7.59 |
| terazosin | 8.04 | 8.6 | 7.44 |
| doxazosin | 8.69 | 9.51 | 7.59 |

TABLE 2b

In Vitro Data for Functional Antagonism at α-1 Adrenoceptors

| Ex. No. | pA$_2$ Dog Prostate [α-1A] | Ex. No. | pA$_2$ Dog Prostate [α-1A] |
|---|---|---|---|
| 4 | 7.91 | 25 | 9.17 |
| 6 | 7.32 | 26 | 9.23 |
| 7 | 7.62 | 27 | 8.63 |
| 14 | 9.01 | 28 | 8.32 |
| 15 | 8.27 | 29 | 8.91 |
| 16 | 7.91 | 30 | 8.94 |
| 17 | 8.94 | 31 | 8.63 |
| 18 | 8.38 | 32 | 7.47 |
| 19 | 8.3 | 34 | 8.98 |
| 20 | 8.83 | 35 | 7.06 |
| 21 | 7.88 | 36 | 8.27 |
| 22 | 8.82 | 37 | 9.62 |
| 23 | 8.32 | 38 | 9.64 |
| 24 | 8.89 | 44 | 8.27 |

IN VIVO DETERMINATION OF INTRAURETHRAL PRESSURE (IUP) IN CANINES

The intraurethral pressure (IUP) model in aged canines is an accepted model of measuring the effect of prostate smooth muscle contraction on urethral tone. Canines also have an enclosed prostate covering the urethral shaft thus providing an anatomical correlate with humans.

Beagle dogs (Marshall Farms) greater that 2 years of age and weighing between 12 and 15 kg were pre-anesthetized with thiopental sodium 15 mg/kg i.v. (Pentothal™, Abbott) and then placed under general anesthesia (isoflurane). A 7F Swan-Ganz balloon catheter (Multiflex - list no. 41224-01, Abbott) was lubricated with a water soluble jelly, inserted into the urethral orifice and advanced approximately 40 cm in male dogs (considerably less in females) until the balloon tip was placed well inside the bladder. The balloon was then inflated with 1 mL of room air and the catheter slowly withdrawn just past the first resistance that is felt at the bladder neck. Preliminary experiments in which dogs were sacrificed after such placement confirmed that this technique results in consistent positioning of the balloon within the prostatic urethra in males or the corresponding location in females. The balloon port of the catheter was connected to a Gould Statham P23Dd pressure transducer interfaced to a computerized data acquisition system (Modular Instruments, Inc., Malvern, Pa.) for the measurement of intraurethral pressure (IUP).

Dogs were then treated with propranolol to block the β-adrenoceptor agonist effects of test agonists. Dose-response curves of the intraurethral pressor effect of epinephrine (EPI) were obtained before and after each of up to 3 increasing doses of a test antagonist (i.v.). Fifteen minutes was allowed after each antagonist dose for equilibration before the next agonist dose-response was initiated. The increase in IUP caused by a given agonist dose was allowed to return to baseline before the next dose was given. The estimated antagonist dissociation constant (in vivo pseudo pA$_2$) was determined by Schild analysis (Brune, et al., Drug Development Research (1995) in press).

The results are shown in Table 3. The results indicate that the compounds of the invention inhibit EPI induced increases in IUP.

TABLE 3

Inhibition of EPI Induced Increase in Canine IUP

| Example | Canine IUP pseudo pA$_2$ |
|---|---|
| 1 | 8.37 |
| 3 | 8.22 |
| 8 | 8.3 |
| 9 | 8.12 |
| 10 | 8.0 |
| 11 | 8.06 |
| 12 | 7.36 |
| 13 | 8.82 |
| prazosin | 7.88 |
| terazosin | 6.91 |
| doxazosin | 6.90 |

SPONTANEOUSLY HYPERTENSIVE RAT (SHR) MODEL

The SHR model historically has been used as a predictor for the hypotensive effects of α-1 adrenoceptor antagonism. Male spontaneously hypertensive rots were anesthetized and the left femoral artery and vein catheterized for the measurement of mean arterial pressure (MAP) and drug administration respectively. The arterial catheter was connected to a Gould Statham p23 ID transducer and the pressure waveform was recorded. MAP (mm Hg) and heart rate (HR, beats/min.) were determined on-line using a BUXCO Cardiovascular Analyzer. After a 30 minute pre-dose control period, each rat was given one dose of a test antagonist i.v. and the MAP and HR were monitored for an additional 2.5 hours. The area under the hypotensive response curve up to 60 minutes post dosing (T$_{60}$ AUC) was determined using a trapezoidal rule integration of the percent change from control arterial pressure dataset.

The results are shown in Table 4. The results show that the compounds of the invention are weakly hypotensive.

TABLE 4

Spontaneously Hypertensive Rat (SHR) Assay

| Example | SHR pseudo pA$_2$ |
|---|---|
| 1 | 6.34 |
| 2 | 6.08 |
| 3 | 5.29 |
| 5 | 5.9 |
| 8 | 6.34 |
| 9 | 6 |
| 10 | 4.8 |
| 12 | 5.22 |
| 13 | 5.44 |
| prazosin | 7.4 |
| terazosin | 6.59 |
| doxazosin | 6.74 |

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous careers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various and bacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular rejection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(othoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case, of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum and release the active compound, Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable career and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than-required for to achieve the desired therapeutic effect and to gradually increase the dosage until the desired effect is achieved.

Generally dosage levels of about 0.01 to about 50, more preferably of about 0.05 to about 5 mg of active compound per kilogram of body weight per day are administered orally to a mammalian patient. If desired, the effective daily dose may be divided into multiple doses for purposes of administration, e.g. two to four separate doses per day.

While the compounds of the invention can be administered as the sole active pharmaceutical agent, they can also be used in combination with a 5-α reductase inhibitor. A particularly preferred 5-α reductase inhibitor for use in coadministration with compounds of the present invention is the compound having the generic name finasteride.

Methods for preparing the compounds of the invention are shown in Schemes I–VI. In the following Schemes, $R_1$ and $R_2$ are independently hydrogen, alkoxy, hydroxy, alkyl, halo, carboxy, or alkoxycarbonyl.

Scheme I illustrates the general procedure for the preparation of the compounds of the invention. Compound 1, prepared by the procedures described in U.S. Pat. No. 4,618,683, which is incorporated herein by reference, is reacted with chloroacetonitrile under mildly basic conditions (for example. diisopropylethylamine, triethylamine and the like) to afford the cyanomethyl compound 2. The nitrile is dissolved in an inert solvent (for example, THF, ether and the like) and treated with a reducing agent (for example, lithium aluminum hydride, diborane or catalytic hydrogenation and the like) to give the ethylene diamine compound 3. The diamine is reacted with the isocyanate 4 of the aromatic compound U, prepared from the aromatic amine by treatment with phosgene or triphosgene, to give the pyrimidine dione 5.

Alternatively as shown in Scheme II, the diamine can by prepared by taking diester 6, prepared by the procedures described in U.S. Pat. No. 5,049,564, which is incorporated herein by reference, in an inert solvent (for example, THF or ether and the like) and reducing the diester with a reducing agent (for example, lithium aluminum hydride or diborane and the like) to give the diol 7. The diol is reacted with an appropriate reagent to form leaving groups (for example, a mesylate or rosylate and the like) giving compound 8.

Treatment of compound 8 with the appropriate diamine ($H_2N$—$(CH_2)_n$—$NH_2$ or synthon) with heating gives the pyrrolidine amine 9. Compound 9 can be further elaborated by the procedures described in Scheme I to give the final compound 10.

The compounds of the invention can also be prepared by the procedures illustrated in Scheme III. Compound 4a is reacted with a haloalkyl isocyanate (for example, 2-chloroethyl isocyanate) by the procedures described in *Eur. J. Med. Chem.* 28: 499 (1993), which is incorporated herein by reference, to give haloalkyl urea 11. Compound 1, as previously described in Scheme I, is reacted with compound 11 to give the final product 5.

The preparation of chiral cis intermediates is shown in Scheme IV. Dihydronaphthylene-1-carboxylic acid 12, is esterified (for example, using diazomethane or alcohol with a trace of sulfuric acid) to give compound 13. Treatment of the α,β-unsaturated ester with lithium cyanide in DMF and acetic acid affords the cyano compound 14. The nitrile ester is hydrolyzed (for example, using KOH in ethanol/water) to give the dicarboxylic acid 15. Treatment of the diacid with acetic anhydride under reflux affords the cyclic art hydrides 16a and 16b. The anhydrides are reacted with optically active (S)-(–)-α-methylbenzylamine to give both the (3aR, 9bR)-compound 18 and the (3aS,9bS)-compound 17 as a mixture of imides separable by crystallization. Compounds 17 and 18 are reduced (for example, with diborane) to give the corresponding N-substituted pyrrolidine compounds 19 and 20. Catalytic hydrogenation affords chiral intermediates 21 and 22. These pyrrolidines can be further elaborated by the procedures described in Schemes I and III to give the final products.

A preferred embodiment is shown in Scheme V. Compound 23 wherein R is a carboxy protecting group is reacted with 2-chloroethyl isocyanate to give urea 24. Compound 24 is reacted with compound 25. in a solvent such as DMSO in the presence of a non-nucleophilic base such as diisopropylethylamine to give the ring closed coupled product 27.

Another preferred embodiment in shown in Scheme VI. The aromatic carboxy-protected amine 28 is reacted with triphosgene to give isocyanate 29. The isocyanate is reacted with amine 30, prepared by the procedure described in Scheme I or II, to cyclize and couple in one step to give compound 31.

Scheme I

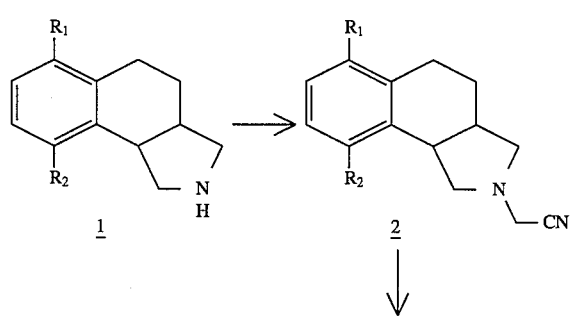

5,521,181
25
-continued
Scheme I
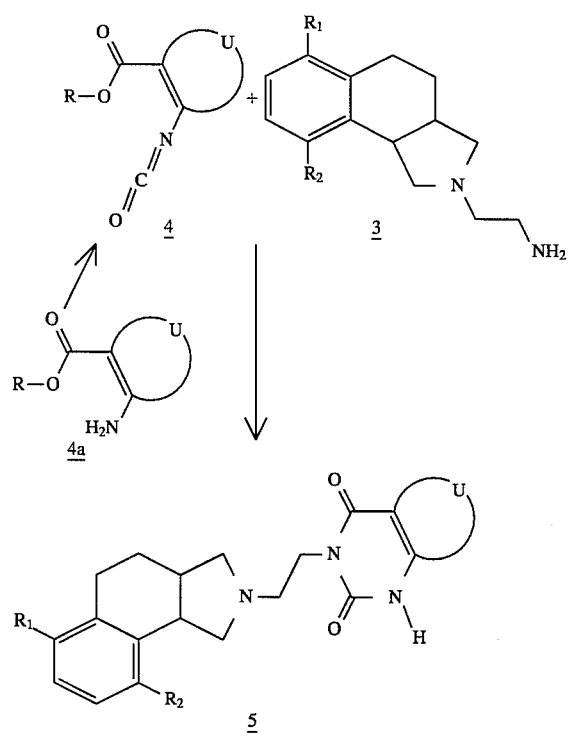
Scheme II
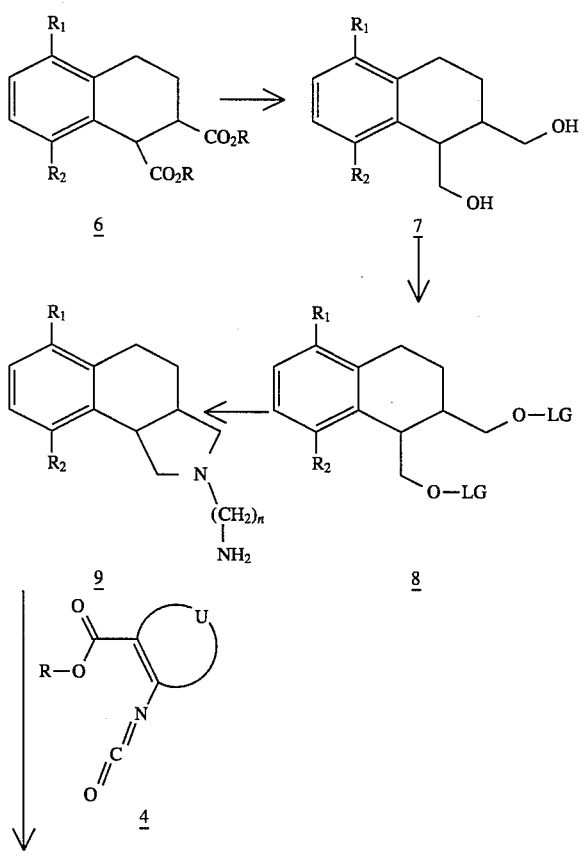
26
-continued
Scheme II
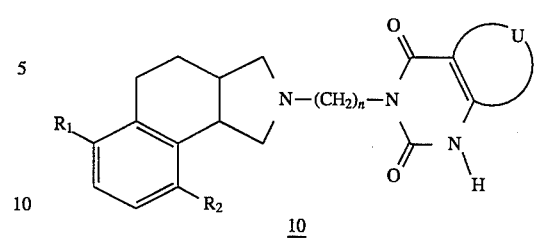
Scheme III
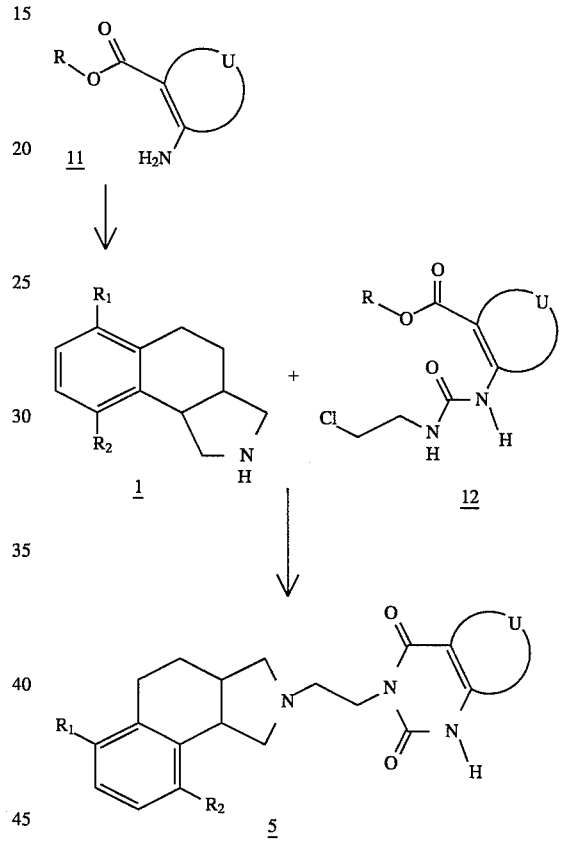

Scheme IV
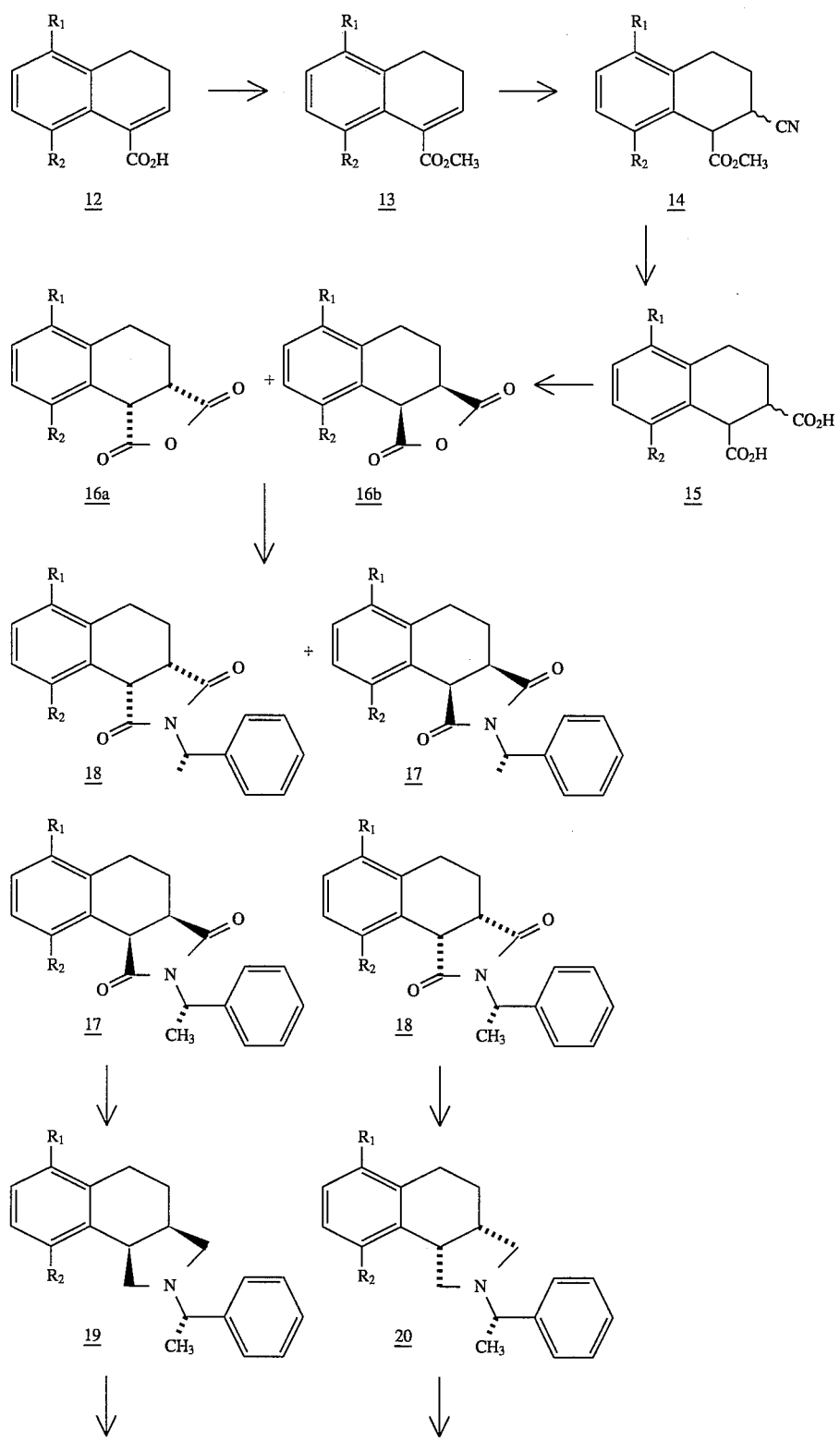

-continued
Scheme IV

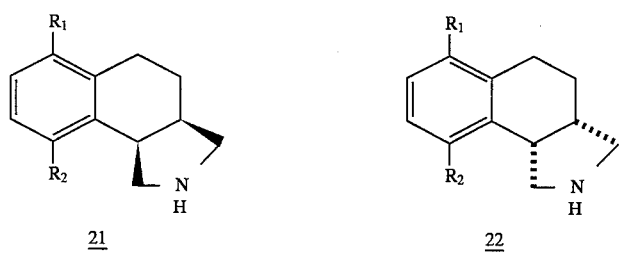

Scheme V

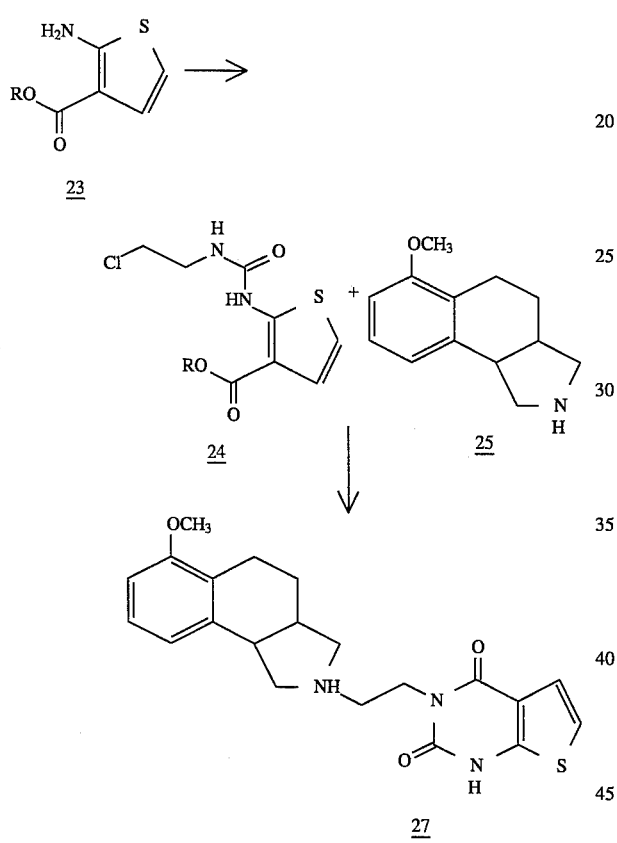

Scheme VI

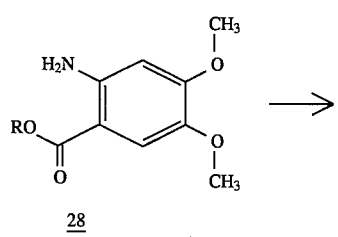

-continued
Scheme VI

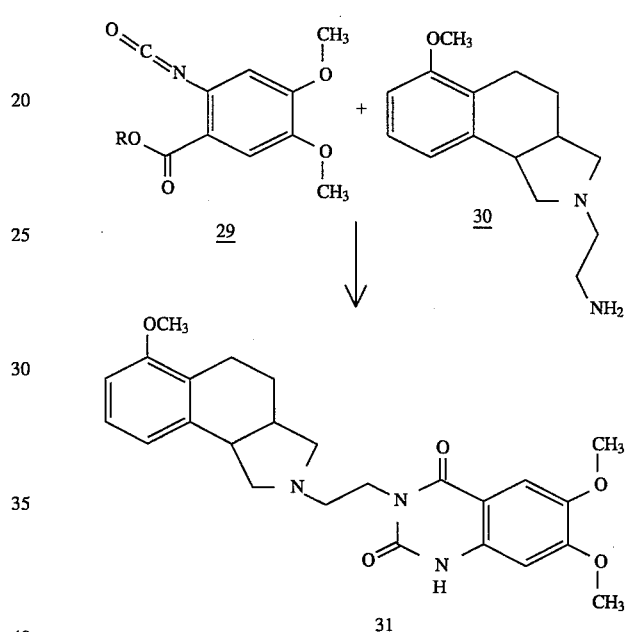

The forgoing may be better understood by reference to the following examples which are provided for illustration and not intended to limit the scope of the inventive concept.

The following abbreviations were used: BH$_3$.DMS for borane dimethylsulfide complex, DMF for dimethylformamide, DMSO for dimethylsulfoxide, Et$_3$N for triethylamine, Et$_2$O for diethyl ether, EtOAc for ethyl acetate, EtOH for ethanol, KOtBu for potassium tert-butoxide, LDA for lithium diisopropylamide, MeOH for methanol, NaOEt for sodium ethoxide, iPrOH for isopropyl alcohol and THF for tetrahydrofuran.

EXAMPLE 1

3-[2-(cis-9-Methoxy-2,3,3a,4,5,9b-hexahydro-[1H]-benz[e]isoindol-1-yl)ethyl][1H,3H]-quinazoline-2,4(1H,3H)-dione hydrochloride

EXAMPLE 1A cis-6-Methoxy-(2-cyanomethyl)-2,3,3a,4,5,9b-hexahydro-[1H]benz[e]isoindole Cis-6-methoxy-2,3,3a,4,5,9b-hexahydro-[1H]benz[e] isoindole (2.39 g, 10 mmol), prepared by the porcedures described in U.S. Pat. No. 4,618,683, which is incorporated herein by reference, and chloroacetonitrile (0.67 mL, 10.6 mmol) were combined in 10 mL acetonitrile and 5 mL ethyldiisopropylamine and heated at 70° C. for 1 h. The reaction was quenched in 5% $NaHCO_3$, and extracted with ethyl acetate (2×). The organic extracts were washed with water (2×) and brine (1×), dried ($Na_2SO_4$) and evaporated toyield 2.20 g of the title compound as an off white solid (90%). $^1$H NMR (300 MHz, $CDCl_3$) δ 1.60 (m, 2H), 1.80 (m, 1H), 2.58 (m, 3H), 2.77 (m, 1H), 3.23 (m, 2H), 3.48 (1, 1H), 3.64 (s, 2H), 3.81 (s, 3H), 6.70 (d, 1H), 6.74 (d, 1h), 7.12 (t, 1H).

EXAMPLE 1B cis-6-Methoxy-(2-(2-aminoethyl))-2,3,3a,4,5,9b-hexahydro-[1H]benz[e]isoindole $LiAlH_4$ (2.40 g, 62 mmol) was suspended in THF (100 mL) and coiled to 0° C. The compound resulting from Example 1A (2.20 g, 9.0 mmol) was dissolved in THF (10 mL) and added dropwsie to the above $LiAlH_4$ suspension. The reaction was then stirred at room temperature for 1.5 hours, quenched by addition of $H_2O$ (2.2 mL), 15% NaOH (2.2 mL), and $H_2O$ (6.6 mL), filtered through celite, washing with several potions of hot THF, adn the solvent evaporated toyield the title compound (2.15 g, 93%) as a colorless oil. $^1$H NMR (300 MHz, $CDCl_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H), 3.40 (m, 1H), 3.80 (s, 3H), 6.67 (d, 1H), 6.75 (d, 1H), 7.11 (t, 1H).

EXAMPLE 1C

3-[2cis(-6-Methoxy,2,3,3a,4,5,9b-hexahydro-1H]-benz[e]isoindol-1-yl)ethyl]-[1H,3H]-quinazoline-2,4(1H,3H)-dione hydrochloride 2-Carboethoxy-phenylisocyanate (0.20 g, 1.0 mmol) was prepared by the reaction of 2-carboethoxyaniline and triphosgene in toluene at reflux, followed by removing the solvent in vacuo. The isocyanate and the compound resulting from Example 1B (0.24 g, 1.0 mmol) were combined in 40 mL of toluene and heated at reflux for 3 hours. The product was then partitioned between 5% $NaHCO_3$ and hot ethyl acetate, and the organic phase was dried ($K_2CO_3$) and evaporated. The resulting product was converted to its hydrochloride salt and recrystallized from ethanol-ether to yield 0.12 g of the title compound as a white solid. $^1$H NMR (300 MHz, DMSO-$d_6$) δ 7.92 (d, 1H), 7.65 (t, 1H), 7.12–7.27 (m, 2H), 7.08 (t, 1H), 6.72 (dd, 2H), 4.02 (t, 2H), 3.73 (s, 3H), 3.12–3.3 (m, 3H), 2.52–2.65 (m, 3H), 2.38–2.48 (m, 2H), 2.1–2.3 (m, 2H), 1.57–1.68 (m, 1H), 1.37–1.5 (m, 1H). Anal calcd for $C_{23}H_{25}N_3O_3.HCl.H_2O$: C, 61.95; H, 6.33; N, 9.42. Found: C, 61.94; H, 6.10; N, 9.18.

EXAMPLE 2

3-[2-(cis-6-Methoxy-2,3,3a,4,5,9-b-hexahydro-[1H]-benz[e]isoindol-1-yl)ethyl]-7-methylthieno[3,2-d]-pyrimidine-2,4(1H,3H)-dione hydrochloride 2-Carbomethoxy-4-methyl-thiophene-3-isocyanate (0.22 g, 1.1 mmol), prepared from the amine and triphosgene by the procedure described in Example 1C, and the compound resulting from Example 1B (0.24 g, 1.0 mmol) were treated by the procedures described in Example 1C to yield 0.12 g of the title compound as a white solid. m.p. 255°–257° C. $^1$H NMR (300 MHz, $CDCl_3$) of the free base δ 1.46–1.58 (m, 1H), 1.69–1.81 (m, 1H), 2.20–2.35 (m, 2H), 2.28 (d, 3H), 2.48–2.60 (m, 2H), 2.64–2.90 (m, 3H), 3.36–3.50 (m, 3H), 3.81 (s, 3H), 4.21 (t, 2H), 6.67 (d, 1H), 6.74 (d, 1H), 7.10 (t, 1H), 7.31 (d, 1H). MS (DCI/$NH_3$) m/e 412 (M+H)$^+$. Anal calcd for $C_{22}H_{25}N_3O_3S.HCl.0.5 H_2O$: C, 57.82; H, 5.96; N, 9.19. Found: C, 58.01; H, 5.95; N, 9.08.

EXAMPLE 3

3-[2-(cis-6-Methoxy-2,3,3a,4,5,9b-hexahydro-[1H]-benz[e]isoindol-1-yl)ethyl]thieno[2,3-d]pyrimidine-2,4(1H,3H)-dione hydrochloride 2-Amino-3-carboethoxythiophene, prepared by the method of Gewald, *Chem. Ber.* 98: 3571 (1965), was treated with 2-chloroethyl-isocyanate by the procedures described by Romeo, et al. in *Eur. J. Med. Chem.*, 28: 499–504 (1993). The resulting urea (0.67 g, 2.4 mmol) and cis-6-methoxy-2,3,3a,4,5,9b-hexahydro-[1H]-benz[e]isoindole (0.45 g, 2.2 mmol), prepared by the procedures described in U.S. Pat. No. 4,618,683, which is incorporated herein by reference, and 0.4 mL diisopropylethylamine in DMSO (1 mL) were heated at 100° C. for 1.5 hours. The reaction was quenched in $H_2O$ and extracted with ethyl acetate. The combined organic extracts were dried and concentrated in vacuo resulting in a urea ester intermediate which was treated with 0.25 mL 1.0M KOtBu in ethanol (2 mL) at reflux for 0.5 hours. After purification by column chromatography eluting with 95:5 ethyl acetate-ethanol and conversion to its HCl salt the title compound (0.30 g, 54%) was obtained as a white solid. m.p. 192°–194° C. $^1$H NMR (500 MHz, DMSO-$d_6$) δ 1.53–1.63 (m, 1H), 1.75–1.82 (m, 1H), 2.38–2.55 (m, 1H), 2.60–2.68 (m, 1H), 2.68–2.78 (m, 1H), 2.91–3.05 (m, 1H), 3.33–3.54 (m, 3H), 3.71–3.86 (m, 1H), 3.78 (s, 3H), 3.93–4.24 (m, 4H), 6.75 (d, 1H), 6.83 (d, 1H), 7.11–7.20 (m, 3H). MS (DCI/$NH_3$) m/e 398 (M+H)$^+$. Anal calcd for $C_{21}H_{23}N_3O_3S.HCl.0.25 H_2O$: C, 57.53; H, 5.63; N, 9.58. Found: C, 57.48; H, 5.68; N, 9.43.

EXAMPLE 4

3-[2-(cis-6-Methoxy-2,3,3a,4,5,9b-hexahydro-[1H]-benz[e]isoindol-1-yl)ethyl]-5-methylthieno[2,3-d]-pyrimidine-2,4(1H,3H)-dione hydrochloride 2-Amino-3-carboethoxy-4-methylthiophene was treated with 2-chloroethylisocyanate by the procedures described in Example 3. The resulting urea (0.35 g, 1.2 mmol) and cis-6-methoxy-2,3,3a,4,5,9b-hexahydro[1H]-benz[e]isoindole (0.23 g, 1.1 mmol) were treated by the procedures described in Example 3 to afford the title compound (0.11 g, 41%) was obtained as a white solid. m.p. 179°–181° C. $^1$H NMR (500 MHz, DMSO-$d_6$) δ 1.40–1.48(m, 1H), 1.60–1.67 (m, 1H), 2.12–2.19 (m, 1H), 2.24 (dd, 1H), 2.34 (s, 3H), 2.41–2.49 (m, 2H), 2.52–2.63 (m, 3H), 3.13 (t, 1H), 3.23–3.30 (m, 2H), 3.75 (s, 3H), 3.94 (t, 2H), 6.64 (s, 1H), 6.72 (d, 1H), 6.74 (d, 1H), 7.08 (t, 1H). MS (DCI/NH$_3$) m/e 412 (M+H)$^+$. Anal calcd for C$_{22}$H$_{25}$N$_3$O$_3$S.HCl.2 H$_2$O: C, 54.59; H, 6.25; N, 8.68. Found: C, 54.30; H, 5.64; N, 8.47.

EXAMPLE 5

3-[2-(cis-6-Methoxy-2,3,3a,4,5,9b-hexahydro-[1H]-benz[e]isoindol-1-yl)ethyl]thieno[3,2-d]pyrimidine-2,4(1H,3H)-dione hydrochloride 3-Amino-2-carboethoxythiophene was treated with 0.33 equivalent as triphosgene by the procedures described in Example 1C. The resulting isocyanate (0.21 g, 1.15 mmol) and the compound resulting from Example 1B (0.24 g, 1.0 mmol) were treated by the procedures described in Example 1C to yield the title compound (0.12 g, 28%) as a white solid. m.p. 190°–192° C. $^1$H NMR (300 MHz, CDCl$_3$) δ 1.55–1.68 (m, 1H), 1.85–1.98 (m, 1H), 2.53–2.65 (m, 1H), 2.70–2.83 (m, 2H), 2.83–2.96 (m, 2H), 3.39–3.50 (m, 2H), 3.67 (q, 1H), 3.82 (s, 3H), 4.08–4.30 (m, 2H), 4.37 (t, 2H), 6.74 (t, 2H), 6.84 (d, 1H), 7.15 (t, 1H), 7.62 (d, 1H), 8.17 (bs, 1H). MS (DCI/NH$_3$) m/e 398 (M+H)$^+$. Anal calcd for C$_{21}$H$_{23}$N$_3$O$_3$S.HCl.0.75 H$_2$O: C, 56.37; H, 5.74; N, 9.39. Found: C, 56.32; H, 5.86; N, 8.90.

EXAMPLE 6

3-[2-(cis-6-Methoxy-2,3,3a,4,5,9b-hexahydro-[1H]-benz[e]isoindol-1-yl)ethyl]-5-phenyl-thieno[2,3-d]pyrimidine-2,4(1H,3H)-dione hydrochloride 2-Amino-3-Carboethoxy-4-phenylthiophene, prepared by the procedure of Gewald, et al, *Chem. Ber.* 94: 99(1966), was treated with 2-chloroethylisocyanate by the procedures described by Romeo, et al. in *Eur. J. Med. Chem.*, 28: 499–504 (1993). The resulting urea (0.59 g, 1.65 mmol) and cis-6-methoxy-2,3,3a,4,5,9b-[1H]-benz[e]isoindole (0.31 g, 1.5 mmol) were treated by the procedures described in Example 3 to yield the title compound (0.15 g, 42%) as a white solid. m.p. 176°–178° C. $^1$H NMR (400 MHz, DMSO-d$_6$) δ 1.49–1.58 (m, 1H), 1.79–1.86 (m, 1H), 2.39–2.47 (m, 1H), 2.54–2.62 (m, 1H), 2.65–2.73 (m, 1H), 2.76–2.93 (m, 1H), 3.12–3.52 (m, 4H), 3.55–3.65 (m, 1H), 3.71–3.83 (m, 1H), 3.75 (s, 3H), 4.05–4.14 (m, 2H), 6.72 (d, 1H), 6.79 (d, 1H), 7.12 (t, 1H), 7.32–7.39 (m, 3H), 7.41 (dd, 2H). MS (DCI/NH$_3$) m/e 474 (M+H)$^+$. Anal calcd for C$_{27}$H$_{27}$N$_3$O$_3$S.HCl. H$_2$O: C, 61.41; H, 5.73; N, 7.96. Found: C, 61.80; H, 5.83; N, 7.81.

EXAMPLE 7

3-[2-(cis-6-Methoxy-2,3,3a,4,5,9b-hexahydro-[1H]-benz[e]isoindol-1-yl)-ethyl]-6-phenyl-thieno[2,3-d]pyrimidine-2,4(1H,3H)-dione hydrochloride 2-Amino-3-Carboethoxy-5-phenylthiophene, prepared by the procedure of Gewald, et at, *Chem. Ber.*, 94: 99 (1966), was treated with 2-chloroethylisocyanate by the procedures described in *Eur. J. Med. Chem.*, 28: 499–504 (1993). The resulting urea (0.42 g, 1.45 mmol) and cis-6-methoxy-2,3,3a,4,5,9b-[1H]-benz[e]isoindole (0.22 g, 1.1 mmol) were treated by the procedures described in Example 3 to yield the title compound (0.11 g, 42%) as a white solid. m.p. 248°–250° C. (dec.). $^1$H NMR (500 MHz, DMSO-d$_6$) δ 1.53–1.64 (m, 1H), 1.74–1.83 (m, 1H), 2.38–2.52 (m, 1H), 2.62–2.78 (m, 2H), 2.94–3.06 (m, 1H), 3.28–3.34 (m, 1H), 3.40–3.54 (m, 3H), 3.77 (s, 3H), 3.79–4.03 (m, 1H), 4.08–4.26 (m, 3H), 6.75 (bs, 1H), 6.83 (d, 1H), 7.16 (t, 1H), 7.32 (t, 1H), 7.42 (t, 2H), 7.61 (s, 1H), 7.67 (d, 2H). MS (DCI/NH$_3$) m/e 474 (M+H)$^+$. Anal calcd for C$_{27}$H$_{27}$N$_3$O$_3$S.HCl.0.5 H$_2$O: C, 62.48; H, 5.63; N, 8.10. Found: C, 62.39; H, 5.58; N, 8.04.

EXAMPLE 8

3-[2-(cis-6-Methoxy-2,3,3a,4,5,9b-hexahydro-[1H]-benz[e]isoindol-1-yl)ethyl]-thieno[3,4-d]-pyrimidine-2,4(1H,3H)-dione hydrochloride 3-Amino-4-carboethoxythiophene, prepared by the method of Baker, et al., *J. Org. Chem.*, 18: 138 (1953), was treated with 0.33 equivalent triphosgene. The resulting isocyanate (0.29 g, 1.6 mmol) and the compound resulting from Example 1B (0.30 g, 1.2 mmol) were treated by the procedure described in Example 1C to yield the title compound (0.15 g, 45%) as a white solid. m.p. 205°–210° C. $^1$H NMR (300 MHz, CDCl$_3$) δ 1.54–1.88 (m, 1H), 1.82–1.94 (m, 1H), 2.52–2.65 (m, 1H), 2.71–2.86 (m, 4H), 3.25–3.38 (m, 2H), 3.66–3.79 (m, 1H), 3.83 (s, 3H), 3.98–4.18 (m, 2H), 4.29 (t, 2H), 6.55 (d, 1H), 6.71 (d, 1H), 6.77 (d, 1H), 7.13 (t, 1H), 8.10 (d, 1H). MS (DCI/NH$_3$) m/e 398 (M+H)$^+$. Anal calcd for C$_{21}$H$_{23}$N$_3$O$_3$S.HCl.1.5 H$_2$O: C, 54.72; H, 5.90; N, 9.12. Found: C, 54.89; H, 5; N, 8.73.

EXAMPLE 9

3-[2-(cis-6-Methoxy-2,3,3a,4,5,9b-hexahydro-[1H]-benz[e]isoindol-1-yl)ethyl]-8-methoxy-quinazoline-2,4(1H,3H)-dione hydrochloride 2-Methoxy-6-carboethoxyaniline was treated with 0.33 equivalent triphosgene. The resulting isocyanate (0.30 g, 1.1 mmol) and the compound resulting from Example 1B (0.25 g, 1.0 mmol) were treated by the procedures described in Example 1C to yield the title compound (0.15 g, 33%) as a white solid. m.p. 233°–235° C. $^1$H NMR (300 MHz, CDCl$_3$ of the free base δ 7.68 (dd, 1H), 7.08–7.2 (m, 3H), 6.75 (t, 2H), 4.42 (m, 2H), 4.1–4.28 (m, 2H), 3.98 (s, 3 H), 3.82 (s, 3H), 3.68 (q, 1H), 3.41 (m, 2H), 2.7–2.98 (m, 4H), 2.51–2.63 (m, 1H), 1.88–1.98 (m, 1H), 1.52–1.68 (m, 1H). MS (DCI/NH$_3$) m/e 422 (M+H)$^+$. Anal calcd for C$_{24}$H$_{27}$N$_3$O$_4$.HCl.1.25 H$_2$O: C, 59.94; H, 5.83; N, 8.74. Found: C, 60.06; H, 5.74; N, 8.73.

EXAMPLE 10

3-[2-(cis-6-Methoxy-2,3,3a,4,5,9b-hexahydro-[1H]-benz[e]isoindol-1-yl)ethyl]-6,7-dimethoxy-quinazoline-2,4(1H,3H)-dione hydrochloride 2-Carboethoxy-4,5-dimethoxyaniline was treated with 0.33 equivalent triphosgene. The resulting isocyanate (0.55 g, 2.2 mmol) and the compound resulting from Example 1B (0.49 g, 2.0 mmol) were treated by the procedures described in Example 1C to yield the title compound (0.60 g, 66%) as a white solid. $^1$H NMR (300 MHz, DMSO-d$_6$) δ 7.3 (d, 1H), 7.18 (t, 1H), 6.7–6.9 (m, 3H), 4.1–4.3 (m, 3H), 3.9–4.1 (m, 1H), 3.85 (s, 3H), 3.8 (s, 3H,), 3.7 (s, 3H), 3.4–3.58 (m, 4H), 2.92–3.6 (m, 2H), 2.6–2.85 (m, 2H), 1.73–1.88 (m, 1H), 1.52–1.68 (m, 1H). MS (DCI/NH$_3$) m/e 452 (M+H)$^+$. Anal calcd for C$_{25}$H$_{29}$N$_3$O$_5$.HCl: C, 61.53; H, 6.20; N, 8.61. Found: C, 61.29; H, 6.28; N, 8.45.

EXAMPLE 11

3-[2-(cis-6-Methoxy-2,3,3a,4,5,9b-hexahydro-[1H]-benz[e]isoindol-1-yl)ethyl]-7-chloro-quinazoline-2,4(1H,3H)-dione hydrochloride 2-Carboethoxy-5-chloroaniline was treated with 0.33 equivalent triphosgene by the procedures described in Example 1C. The resulting isocyanate (0.26 g, 1.25 mmol) and the compound resulting from Example 1B (0.25 g, 1.0 mmol) were is treated by the procedures described in Example 1C to yield the title compound (0.12 g, 25%) as a white solid. m.p. >250° C. (dec.). $^1$H NMR (300 MHz, DMSO-d$_6$) δ 7.95 (t, 1H), 7.28 (m, 2H), 7.18 (t, 1H), 6.84 (m, 1H), 6.75 (t, 1H), 3.95– 4.3 (m, 4H), 3.78 (s, 3H), 3.42–3.58 (m, 4H), 2.92–3.1 (m, 2H), 2.62–2.85 (m, 2H), 1.7–1.86 (m, 1H), 1.52–1.68 (m, 1H). MS (DCI/NH$_3$) m/e 426 (M+H)$^+$. Anal calcd for C$_{23}$H$_{24}$N$_3$O$_3$Cl.HCl.0.25 H$_2$O: C, 59.17; H, 5.51; N, 9.00. Found: C, 59.10; H, 5.52; N, 8.95.

EXAMPLE 12

3-[2-(cis-6-Methoxy-2,3,3a,4,5,9b-hexahydro-[1H]-benz[e]isoindol-1-yl)ethyl]-5-methyl-quinazoline-2,4(1H,3H)-dione hydrochloride 2-Carbomethoxy-3-methylaniline was treated with 0.33 equivalent triphosgene by the procedures described in Example 1C. The resulting isocyanate (0.28 g, 1.4 mmol) and the compound resulting from Example 1B (0.28 g, 1.1 mmol) were treated as described by the procedures described in Example 1C to yield the title compound (0.16 g, 28%) as a white solid. m.p. 178°–180° C. $^1$H NMR (300 MHz, CDCl$_3$) of the free base δ 7.38 (t, 1H), 7.17 (t, 1H), 6.92 (dd, 2H), 6.72 (dd, 2H), 4.12–4.42 (m, 4H), 3.82 (s, J=3, 3.68, q Hz, 1H), 3.4–3.58 (m, 2H), 2.93–3.06 (m, 2H), 2.7–2.85 (m, 2H), 2.73 (s, 3H), 2.51–2.65 (m, 1H), 1.87–2.0 (m, 1H), 1.53–1.7 (m, 1H). MS (DCI/NH$_3$) m/e 406 (M+H)$^+$. Anal calcd for C$_{24}$H$_{27}$N$_3$O$_3$.HCl.H$_2$O: C, 62.67; H, 6.57; N, 9.14. Found: C, 62.72; H, 6.17; N, 9.08.

EXAMPLE 13

3-[2-((3aR,9bR)-cis-6-Methoxy-2,3,3a,4,5,9b-hexahydro-[1H]-benz[e]isoindol-1-yl)ethyl]-thieno[2,3-d]pyrimidine-2,4(1H,3H)-dione hydrochloride

EXAMPLE 13A

5-Methoxy-3,4-dihydronaphthalene-1-carboxylic acid methyl ester

5-Methoxy-3,4-dihydronaphthalene-1-carboxylic acid (100 g, 490 mmol) was dissolved in 800 mL of methanol and 20 mL of 96% H$_2$SO$_4$, and heated at reflux for 18 hours. The reaction was then cooled and evaporated under reduced pressure to a volume of 100 mL, and quenched on ice. The aqueous mixture was extracted with diethyl ether (3×100 mL), and the organic phase was washed with water, 5% aqueous NaHCO$_3$, brine, and then dried (MgSO$_4$) and evaporated to yield 101 g (94%) of the title compound as a colorless oil. $^1$H NMR (300 MHz, CDCl$_3$) δ 2.36 (m, 2H), 2.78 (t, 3H), 3.83 (s, 6H), 6.82 (d, 1H), 7.14 (t, 1H), 7.19 (t, 1H), 7.40 (t, 1H).

EXAMPLE 13B

5-Methoxy-2-cyano-1,2,3,4-tetrahydrohaphthalene-1-carboxylic acid methyl ester A solution of 1100 mL 0.5M LiCN (550 mmol) in DMF and acetic acid (27.7 mL, 483 mmol) was prepared. The product resulting from Example 13A (101 g, 0.460 mmol) was dissolved in 100 mL DMF, and added over 15 minutes to the above solution. The reaction was stirred at 25° C. for 3.5 hours, and then poured onto ice/H$_2$O (5000 mL). The aqueous mixture was extracted with ether (3×500 mL), and the organic extracts were washed with H$_2$O and brine, dried (MgSO$_4$) and evaporated to dryness to yield 103.4 g (92%) of a light yellow oil as a mixture of cis and trans isomers of the desired product. $^1$H NMR (300 MHz, CDCl$_3$) δ 2.00–2.38 (m, 2H), 2.50–3.10 (m, 2H), 3.30–3.52 (m, 1H), 3.77 (s, 3H), 3.83 (s, 3H), 4.07 (m, 1H), 6.77 (d, 1H), 6.89 (d, 1H), 7.27 (m, 1H).

EXAMPLE 13C

5-Methoxy-1,2,3,4-tetrahydronaphthalene-1,2-dicarboxylic acid

The nitrile ester resulting from Example 13B (103 g, 422 mmol) was dissolved in 700 mL ethanol and 700 mL 45% aqueous KOH, and the reaction was heated at reflux for 10 hours. The cooled solution was diluted with 1.5 kg of ice and acidified to pH 1 with concentrated aqueous HCl. The resulting product was as collected by filtration, washed with H$_2$O (3×200 mL) and dried under vacuum to yield 65.3 g (62%) of the title compound as a white solid. m.p. 200°–201° C. $^1$H NMR (300 MHz, CD$_3$OD) δ 1.85 (m, 1H), 2.27 (m, 1H), 2.65 (m, 1H), 2.85 (m, 1H), 3.10 (m, 1H), 3.80 (s, 3H), 4.05 (d, 1H), 6.79 (d, 1H), 6.92 (d, 1H), 7.11 (t, 1H).

EXAMPLE 13D

5-Methoxy, 1,2,3,4-tetrahydronaphthalene-1,2-dicarboxylic anhydride

The compound resulting from Example 13C (65.3 g, 260 mmol) was dissolved in acetic anhydride (400 mL) and heated at reflux for 4 hours. The solvent was evaporated, and the resulting solid was triturated with 1:1 hexane:diethyl ether, and then collected and dried to yield 48.9 g (81%) of the title compound as a white solid. m.p. 138°–140° C. $^1$H NMR (300 MHz, CDCl$_3$) δ 1.97 (m, 1H), 2.28 (m, 1H), 2.47 (m, 1H), 2.95 (m, 1H), 3.55 (m, 1H), 3.83 (s, 3H), 4.32 (d, 1H), 6.83 (d, 1H), 7.17 (d, 1H), 7.27 (t, 1H).

EXAMPLE 13E

(3aR,9bR)-6-Methoxy-((S)-α-methylbenzyl)-2,3,3a,4,-5,9b-[1H]-hexahydrobenz[e]isoindole-1,3-dione
and
(3aS,9bS)-6-Methoxy-((S)-α-methylbenzyl)-2,3,3a,4,-5,9b-[1H]-hexahydrobenz[e]isoindole-1,3-dione The compound resulting from Example 13D (48.8 g, 210 mmol) was combined with (S)-(−)-α-methylbenzyl amine (28.1 g, 0.230 mmol) in xylene (200 mL), and the reaction was heated to reflux with water removal (Dean Stark trap) until the theoretical amount of water was removed. The reaction was then cooled and diluted with ethyl acetate (300 mL). The resulting solution was washed with 5% aqueous HCl, 5% aqueous NaHCO$_3$ and brine, dried (MgSO$_4$) and evaporated to dryness. The resulting oily solid was triturated with diethyl ether, and the resulting crystalline title compound was collected. (28.14 g, 81%) of the (3aR,9bR) product. m.p. 148°–150° C. $^1$H NMR (300 MHz, CDCl$_3$) δ 1.75 (d, 3H), 1.80 (m, 1H), 2.20 (m, 2H), 2.89 (m, 1H), 3.20 (m, 1H), 3.80 (s, 3H), 3.95 (d, 1H), 5.49 (q, 1H), 6.79 (d, 1H), 7.17–7.45 (m, 7H). From the mother liquor, on cooling, a second crop was collected (16.8 g, 48%) and shown to be the (3aS,9bS) product. m.p. 101°–103° C. $^1$H NMR (300 MHz, CDCl$_3$) δ 1.78 (d, 3H), 1.85 (m, 1H), 2.20 (m, 2H), 2.88 (m, 1H), 3.17 (m, 1H), 3.81 (s, 3H), 3.98 (d, 1H), 5.48 (q, 1H), 6.78 (d, 1H), 7.17–7.42 (m, 7H).

EXAMPLE 13F (3aR,9bR)-6-Methoxy-((S)-α-methylbenzyl)-2,3,3a,4,- 5,9b-[1H]-hexahydrobenz[e]isoindole hydrochloride The (3aR,9bR) compound resulting from Example 13E (28.0 g, 83.5 mmol) was dissolved in THF (100 mL) and added over 5 minutes to a 1.0M solution of BH$_3$ in THF. The reaction mixture was heated at reflux for 2 hours, and then cooled to 25° C. Methanol (100 mL) was added cautiously, and after evolution of H$_2$ ceased, solvent was evaporated at reduced pressure. The resulting oil was dissolved in 2:1 methanol:isopropyl alcohol saturated with HCl (g), and the resulting solution was heated at reflux for 3 hours. The solvent was removed in vacuo, the resulting solid was triturated with 1:1 ethanol:diethyl ether, and the title compound (25.8 g, 90%) was collected by filtration. m.p. 229°–231° C. $^1$H NMR (300 MHz, CDCl$_3$) of the free base δ 1.38 (d, 3H), 1.49 (m, 1H), 1.57 (m, 1H), 2.07 (dd, 1H), 2.15 (m, 1H), 2.40–2.72 (m, 3H), 2.97 (dd, 1H), 3.21 (q, 1H), 3.49 (m, 2H), 3.81 (s, 3H), 6.68 (d, 1H), 6.77 (d, 1H), 7.11 (t, 1H), 7.19–7.38 (m, 5H).

EXAMPLE 13G (3aR,9bR)-6-Methoxy-2,3,3a,4,5,9b-[1H]-hexahydrobenz[e]isoindole hydrochloride The compound resulting from Example 13F (25.7 g, 74.7 mmol) was dissolved in methanol (700 mL) and 10% Pd/C (5.9 g) was added. The reaction was hydrogentated at 4 atmospheres of hydrogen at room temperature for 24 hours. The catalyst was removed by filtration, and the solvent was evaporated to yield 15.9 g (89%) of the title compound as a white solid. m.p. 223°–225° C. $^1$H NMR (300 MHz, CD$_3$OD) δ 1.60 (m, 1H), 1.93 (m, 1H), 2.54 (m, 1H), 2.67 (m, 1H), 2.93 (m, 1H), 3.09 (dd, 1H), 3.13 (dd, 1H), 3.53 (m, 1H), 3.58 (dd, 1H), 3.67 (dd, 1H), 3.80 (s, 3H), 6.78 (d, 1H), 6.81 (d, 1H), 7.16 (t, 1H). [α]$_D$$^{20}$=–22.0° (c=1.39, MeOH, free base).

EXAMPLE 13H

3-[2-((3aR,9bR)-cis-6-Methoxy-2,3,3a,4,5,9b-hexahydro-[1H]-benz[e]isoindol-1-yl)ethyl]-thieno-[2,3-d]pyrimidine-2,4(1H,3H)-dione hydrochloride 2-Amino-3-carboethoxythiophene, prepared by the method of Gewald, *Chemische Berichte*, 98: 3571 (1965), was treated with 2-chloroethyl-isocyanate by the procedures described in *Eur. J. Med. Chem.* 28: 499 (1993). The resulting urea (1.65 g, 6.0 mmol) and the product from Example 13G (1.10 g, 5.4 mmol) were treated by the procedures described in Example 3 to yield 0.91 g (39%) of the title compound as a white solid. m.p. 179°–182° C. (dec.). $^1$H NMR (300 MHz, CDCl$_3$) δ 1.52–1.66 (m, 1H), 1.80–1.92 (m, 1H), 2.49–2.65 (m, 3H), 2.69–2.83 (m, 2H), 3.18–3.38 (m, 2H), 3.59–3.70 (m, 1H), 3.82 (s, 3H), 3.96–4.10 (m, 2H), 4.3 (bt, 2H), 6.49 (d, 1H), 6.70 (d, 1H), 6.79 (d, 1H), 6.93 (d, 1H), 7.13 (t, 1H). MS (DCI/NH$_3$) m/e 398 (M+H)$^+$. Anal calcd for C$_{21}$H$_{23}$N$_3$O$_3$S.HCl.1.5 H$_2$O: C, 54.72; H, 5.90; N, 9.12. Found: C, 55.03; H, 6.03; N, 8.83.

EXAMPLE 13I (3aR,9bR)-2-Cyanomethyl-6-methoxy-2,3,3a,4,5,9b-[1H]-hexahydrobenz[e]isoindole The compound resulting from Example 13G (2.39 g, 10.0 mmol) was dissolved in H$_2$O, basified to pH 12 with aqueous NaOH solution and extracted 3×CH$_2$Cl$_2$. The organic extracts were dried (K$_2$CO$_3$), and evaporated to yield 1.96 g (9.64 mmol) of the free base. To the free base dissolved in CH$_3$CN (10 mL) and diisopropylethylamine (5 mL) was added 0.67 mL (10.6 mmol) of chloroacetonitrile. The reaction was heated at 70° C. for 1 hour, quenched in 5% NaHCO$_3$, and extracted with ethyl acetate (2×). The organic extracts were washed with water (2×) and brine (1×), dried (Na$_2$SO$_4$) and evaporated to yield 2.20 g of the title compound as an off white solid (90.5%). $^1$H NMR (300 MHz, CDCl$_3$) δ 1.60 (m, 2H), 1.80 (m. 1H), 2.58 (m, 3H), 2.77 (m, 1H), 3.23 (m, 2H), 3.48 (q, 1H), 3.64 (s, 2H), 3.81 (s, 3H), 6.70 (d, 1H), 6.74 (d, 1H), 7.12 (t, 1H).

EXAMPLE 13J (3aR,9bR)-2-Aminoethyl-6-methoxy-2,3,3a4,5,9b-[1H]-hexahydrobenz[e]isoindole LiAlH$_4$ (0.82 g, 21.5 mmol) was suspended in THF (30 mL) and cooled to 0° C. The compound resulting from Example 13I (0.80 g, 3.30 mmol) was dissolved in THF (5 mL) and added dropwise to the above LiAlH$_4$ suspension. The reaction was then stirred at room temperature for 1.5 hours, quenched by addition of H$_2$O (0.8 mL), 15% NaOH (0.8 mL) and H$_2$O (2.4 mL), filtered through celite, washing with several hot portions of THF, and the solvent evaporated to yield the title compound (0.75 g, 93%) as a colorless oil. $^1$H NMR (300 MHz, CDCl$_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H, 3.40 (m, 1H), 3.80 (s, 3H), 6.67 (d, 1H), 6.75 (d, 1H), 7.11 (t, 1H).

EXAMPLE 14

3-[2-(cis-6-Methoxy-2,3,3a,4,5,9b-hexahydro-[1H]-benz[e]isoindol-1-yl)ethyl]-7-carbomethoxy-quinazoline-2,4(1H,3H)-dione hydrochloride 2,5-Bis-carbomethoxyaniline was treated with 0.33 equivalent triphosgene by the procedures described in Example 1C. The resulting isocyanate (0.60 g, 2.4 mmol) and the compound resulting from Example 1B (0.48 g, 1.9 mmol) were treated by the procedures described in Example 1C to yield the title compound (0.38 g, 37%) as a white solid. m.p. 230°–233° C. (dec.). $^1$H NMR (300 MHz, DMSO-d$_6$) δ 8.08 (d, 1H), 7.81 (s, 1H), 7.72 (d, 1H), 7.18 (t, 1H), 6.82 (d, 1H), 6.75 (d, 1H), 4.18–4.3 (m, 2H), 3.92 (s, 3H), 3.78 (s, 3H), 3.4–3.6 (m, 4H), 2.85–3.1 (m, 2H), 2.55–2.85 (m, 4H), 1.7–1.83 (m, 1H), 1.52–1.65 (m, 1H). MS (DCI/NH$_3$) m/e 450 (M+H)$^+$. Anal calcd for C$_{25}$H$_{27}$N$_3$O$_5$.HCl.0.5 H$_2$O: C, 60.66; H, 5.91; N, 8.49. Found: C, 60.91; H, 5.79; N, 8.39.

EXAMPLE 15

3-[2-(cis-6-Methoxy-2,3,3a,4,5,9b-hexahydro-[1H]-benz[e]isoindol-yl)ethyl]-6-fluoro-quinazoline-2,4(1H,3H)-dione hydrochloride 2-Carboethoxy-4-fluoroaniline was treated with 0.33 equivalent triphosgene by the procedures described in Example 1C. The resulting isocyanate (0.46 g, 2.2 mmol) and the compound resulting from Example 1B (0.46. g, 1.9 mmol) were treated by the procedures described in Example 1C to yield the title compound (0.44 g, 55%) as a white solid. m.p. 208°–210° C. (dec). $^1$H NMR (300 MHz, DMSO-d$_6$) δ 7.55–7.7 (m, 2H), 7.28 (m, 1H), 7.17 (t, 1H), 6.71–6.88 (m, 2H), 3.95–4.33 (m, 3H), 3.87 (s, 3H), 3.68–3.75 (m, 1H), 3.4–3.58 (m, 4H), 2.92–3.08 (m, 1H), 2.58–2.85 (m, 2H), 2.32–2.48 (m, 1H), 1.7–1.87 (m, 1H), 1.5–1.7 (m, 1H). MS (DCI/NH$_3$) m/e 410 (M+H)$^+$. Anal calcd for C$_{23}$H$_{24}$N$_3$O$_3$F.HCl.0.5 H$_2$O: C, 60.72; H, 5.76; N, 9.24. Found: C, 60.35; H, 5.75; N, 9.04.

EXAMPLE 16

3-[2-(cis-6-Methoxy-2,3,3a,4,5,9b-hexahydro-[1H]-benz[e]isoindol-yl)ethyl]-6-nitro-quinazoline-2,4(1H,3H)-dione hydrochloride 2-Carboethoxy-4-nitroaniline was treated with 0.33 equivalent triphosgene by the procedures described in Example 1C. The resulting isocyanate (0.48 g, 2.1 mmol) and the compound resulting from Example 1B (0.46 g, 1.9 mmol) were treated by the procedures described in Example 1C to yield the title compound (0.18 g, 25%) as a white solid. m.p. >250° C. (dec.). $^1$H NMR (300 MHz, DMSO-d$_6$) δ 8.62 (d, 1H), 8.48 (dd, 1H), 7.32 (d, 1H), 7.08 (t, 1H), 6.72 (d, 2H), 4.03 (t, 2H), 3.73 (s, 3H), 3.18–3.25 (m, 4H), 2.4–2.7 (m, 4H), 2.22–2.32 (m, 2H), 1.37–1.53 (m, 1H), 1.6–1.7 (m, 1H). MS (DCI/NH$_3$) m/e 436 (M+H)$^+$. Anal calcd for C$_{23}$H$_{24}$N$_4$O$_5$.HCl.0.25 H$_2$O: C, 57.86; H, 5.38; N, 11.73. Found: C, 57.87; H, 5.35; N, 11.50.

EXAMPLE 17

3-[2-(cis-6-Methoxy-2,3,3a,4,5,9b-hexahydro-[1H]-benz[e]isoindol1-yl)ethyl]-6-methoxy-quinazoline-2,4(1H,3H)-dione hydrochloride 2-Carboethoxy-4-methylaniline was treated with 0.33 equivalent triphosgene by the procedures described in Example 1C. The resulting isocyanate (0.33 g, 1.5 mmol) and the product from Example 1B (0.32 g, 1.3 mmol) were treated by the procedures described in Example 1C to yield the title compound (0.129 g, 25%) as a white solid. m.p. 159°–161°; $^1$H NMR (300 MHz, DMSO-d$_6$) δ 7.35 (m, 2H), 7.18 (m, 2H), 6.7–6.88 (m, 2H), 3.98–4.18 (m, 3H), 3.8 (s, 3H), 3.78 (s, 3H), 3.6–3.8 (m, 1H), 3.4–3.6 (m, 4H), 2.95–3.1 (m, 2H), 2.6–2.85 (m, 2H), 1.7–1.9 (m, 1H), 1.55–1.68 (m, 1H). MS (DCI/NH$_3$) m/e 422 (M+H)$^+$. Anal calcd for C$_{24}$H$_{27}$N$_3$O$_4$.HCl.H$_2$O: C, 60.56; H, 6.35; N, 8.83. Found: C, 60.54; H, 6.33; N, 8.55.

EXAMPLE 18

3-[2-(cis-6-Methoxy-2,3,3a,4,5,9b-hexahydro-[1H]-benz[e]isoindol-1-yl)ethyl]-6,7,8-trimethoxy-quinazoline-2,4(1H,3H)-dione hydrochloride 2,3,4-Trimethoxy-6-carbomethoxyaniline was treated with 0.33 equivalent triphosgene by the procedures described in Example 1C. The resulting isocyanate (0.50 g, 2.0 mmol) and the compound resulting from Example 1B (0.46 g, 1.9 mmol) were treated by the procedures described in Example 1C to yield the title compound (0.22 g, 25%) as a white solid. m.p. 205°–207° C. $^1$H NMR (300 MHz, DMSO-d$_6$) δ 7.12–7.25 (m, 2H), 6.71–6.88 (m, 2H), 3.95–4.3 (m, 4H), 3.88 (s, 3H), 3.85 (s, 3H), 3.82 (s, 3H), 3.78 (s, 3H), 3.42–3.57 (m, 4H), 2.93–3.08 (m, 1H), 2.62–2.83 (m, 2H), 2.34–2.48 (m, 1H), 1.72–1.87 (m, 1H), 1.52–1.68 (m, 1H). MS (DCI/NH3) m/e 482 (M+H)$^+$. Anal calcd for C$_{26}$H$_{31}$N$_3$O$_5$.HCl. 0.25H$_2$O: C, 59.77; H, 6.27; N, 8.04. Found: C, 59.69; H, 6.30; N, 7.96.

EXAMPLE 19

3-[2-(cis-6-Methoxy-2,3,3a,4,5,9b-hexahydro-[1H]-benz[e]isoindol-1-yl)ethyl]-8-methyl-quinazoline-2,4(1H,3H)-dione hydrochloride 2-Carboethoxy-6-methylaniline was treated with 0.33 equivalent triphosgene by the procedures described in Example 1C. The resulting isocyanate (0.40 g, 2.0 mmol) and the compound resulting from Example 1B (0.46 g, 1.6 mmol) were treated by the procedures described in Example 1C to yield the title compound (0.12 g, 18%) as a white solid. m.p. 250°–252° C. (dec.). $^1$H NMR (300 MHz, DMSO-d$_6$) of the free base δ 7.8 (d, 1H), 7.5 (d, 1H), 7.05–7.13 (m, 2H), 6.72 (dd, 2H), 4.02 (t, 2H,), 3.72 (t, 3H), 3.12–3.3 (m, 3H), 2.52–2.7 (m, 4H), 2.38–2.49 (m, 1H), 2.35 (s, 3H), 2.1–2.25 (m, 2H), 1.58–1.7 (m, 1H), 1.37–1.5 (m, 1H). MS (DCI/NH$_3$) m/e 406 (M+H)$^+$. Anal calcd for C$_{24}$H$_{27}$N$_3$O$_3$.HCl.0.25 H$_2$O: C, 64.57; H, 6.43; N, 9.41. Found: C, 64.63; H, 6.36; N, 9.42.

EXAMPLE 20

3-[2-(cis-6-Methoxy-2,3,3a4,5,9b-hexahydro-[1H]-benz[e]isoindol-1-yl)ethyl]-6,8-dimethyl-quinazoline-2,4(1H,3H)-dione hydrochloride 2-Carboethoxy-4,6-dimethylaniline was treated with 0.33 equivalent triphosgene by the procedures described in Example 1C. The resulting isocyanate (0.45 g, 2.1 mmol) and the compound resulting from Example 1B (0.46 g, 1.6 mmol) were treated by the procedures described in Example 1C to yield the title compound (0.22 g, 30%) as a white solid. m.p. 273°–4° C. (dec). $^1$H NMR (300 MHz, DMSO-d$_6$) δ 7.62 (s, 1H), 7.39 (s, 1H), 7.18 (t, 1H), 6.7–6.9 (m, 2H), 4.2–4.3 (m, 2H), 4.08–4.2 (m, 1H), 3.8–4.1 (m, 1H), 3.8 (s, 1H), 3.4–3.58 (m, 4 H), 2.88–3.1 (m, 2H), 2.6–2.83 (m, 2H), 2.33 (s, 3H), 2.3 (s, 3H), 1.72–1.85 (m, 1H), 1.48–168 (m, 1H). MS (DCI/NH$_3$) m/e 420 (M+H)$^+$. Anal calcd for C$_{25}$H$_{29}$N$_3$O$_3$.HCl: C, 65.85; H, 6.63; N, 9.22. Found: C, 65.60; H, 6.59; N, 9.03.

EXAMPLE 21

3-[2-(cis-6-Methoxy-2,3,3a,4,5,9b-hexahydro-[1H]-benz[e]isoindol-1-yl)ethyl]-pyrido[2,3-d]pyrimidine-2,4(1H,3H)-dione hydrochloride 2-Amino-3-ethoxycarbonylpyridine (0.46 g, 2.8 mmol), prepared from 2-aminonicotinic acid by the procedure described in *J. Chem. Soc.*, 1045 (1956) for 3-aminopicolinic acid, and Et$_3$N (0.74 mL, 53 mmol) were taken up in anhydrous as CH$_2$Cl$_2$ under N$_2$ and cooled to −78° C. Phosgene (1.5 mL of 1.93M solution in toluene, 2.8 mmol) was added, and the reaction was stirred at −78° C. for 45 minutes and at 25° C. for 1.5 hours. The compound resulting from Example 1B in 4 mL of CH$_2$Cl$_2$ was added, and the reaction was stirred for 2 hours. The reaction mixture was partitined between 1M NaOH and CH$_2$Cl$_2$. The CH$_2$Cl$_2$ layer was dried (MgSO$_4$), filtered, concentrated in vacuo and taken up in THF (30 mL). To this solution was added 6 mL of 1M potassium tert-butoxide in THF. The reaction was stirred for 1 hour at 25° C. and then was concentrated and chromatographed eluting with 5% EtOH in CH$_2$Cl$_2$ sainted with NH$_3$ increasing the EtOH concentration to 10%. The product (0.45 g, 40%) was converted to its HCl salt which was recrystallized from EtOH/Et$_2$O. m.p. 234°–236° C. $^1$H NMR (300 MHz, CDCl$_3$) of the free base δ 1.47–1.61 (m, 1H), 1.72–1.86 (m, 1H), 2.27 (q, 2H), 2.49–2.61 (m, 1H), 2.64–2.77 (m, 2H), 2.84–2.95 (m, 1H), 3.05–3.16 (m, 1H), 3.53 (q, 1H), 3.76 (t, 2H), 3.80 (s, 3H), 4.17–4.35 (m, 2H), 6.67 (d, 1H), 6.77 (d, 1H), 6.90–6.96 (m, 1H), 7.09 (t, 1H), 8.05 (dt, 1H), 8.48 (dd, 1H). MS (DCI/NH$_3$) m/e 393 (M+H)$^+$. Anal calcd for C$_{22}$H$_{24}$N$_4$O$_3$.HCl.0.75 H$_2$O: C, 59.73; H, 6.04; N, 12.66. Found: C, 59.57; H, 5.96; N, 12.39.

EXAMPLE 22

3-[2-(cis-6-Methoxy-2,3,3a,4,5,9b-hexahydro-[1H]-benz[e]isoindol-1-yl)ethyl]-pyrido[3,2-d]pyrimidine-2,4(1H,3H)-dione hydrochloride Following the procedure described for Example 21, 3-amino-2-ethoxycarbonylpyridine (0.30 g, 1.8 mmol), prepared by the method described in *J. Chem. Soc.*, 1045 (1956), Et$_3$N (0.48 mL, 3.4 mmol), phosgene (0.93 mL, 1.93 M in toluene, 1.8 mmol), and the compound resulting from Example 1B (0.40 g, 1.6 mmol) provided 0.51 g (80%) of the desired product which was converted to its HCl salt. m.p. 195°–198° C. $^1$H NMR (300 MHz, CDCl$_3$) of the free base δ 1.47–1.62 (m, 1H), 1.74–1.87 (m, 1H), 2.47 (t, 2H), 2.50–2.76 (m, 3H), 2.97–3.07 (m, 1H), 3.13–3.25 (m, 1H), 3.46 (q, 1H), 3.70–3.83 (m, 2H), 3.78 (s, 3H), 4.24–4.43 (m, 2H), 6.65 (d, 1H), 6.77 (d, 1H), 7.07 (d, 1H), 7.12 (d, 1H), 7.31 (dd, 1H), 8.25 (d, 1H). MS (DCI/NH$_3$) m/e 393 (M+H)$^+$. Anal calcd for C$_{22}$H$_{24}$N$_4$O$_3$. HCl.1.25 H$_2$O: C, 58.53; H, 6.14; N, 12.41. Found: C, 58.50; H, 5.83; N, 12.32.

EXAMPLE 23

3-[2-(cis-6-Methoxy-2,3,3a,4,5,9b-hexahydro-[1H]-benz[e]isoindol-1-yl)ethyl]-5-chloro-quinazoline-2,4(1H,3H)-dione hydrochloride 2-Carboethoxy-3-chloroaniline was treated with 0.33 equivalent triphosgene by the procedures described in Example 1C. The resulting isocyanate (0.44 g, 2.1 mmol) and the compound resulting from Example 1B (0.40 g, 1.6 mmol) were treated by the procedures described in Example 1C to yield the title compound (0.12 g, 18%) as a white solid. m.p. >250° C. (dec). $^1$H NMR (300 MHz, CDCl$_3$) of the free base δ 7.35 (m, 2H), 7.18 (m, 2H), 7.0 (d, 2H), 6.73 (dd, 2H), 4.1–4.42 (m, 4H), 3.82 (s, 3H), 3.68 (q, 1H), 3.4–3.57 (m, 2H,), 2.87–3.0 (m, 2H), 2.7–2.84 (m, 2H), 2.52–2.65 (m, 1H), 1.87–1.98 (m, 1H), 1.55–1.7 (m, 1H). MS (DCI/NH$_3$) m/e 426 (M+H)$^+$. Anal calcd for C$_{23}$H$_{24}$N$_3$O$_3$Cl.HCl.2 H$_2$O: C, 55.43; H, 5.86; N, 8.43. Found: C, 55.73; H, 5.60; N, 8.31.

EXAMPLE 24

3-[2-(cis-6-Methoxy-2,3,3a,4,5,9b-hexahydro-[1H]-benz[e]isoindol-1-yl)ethyl]-pyrido[3,4-d]pyrimidine-2,4(1H,3H)-dione dihydrochloride Following the procedure described for Example 21, 3-amino-4-ethoxycarbonylpyridine (0.58 g, 3,5 mmol), prepared by substituting 3,4-pyridinedicarboximide for quinolinimide and the procedure described in *J. Chem. Soc.*, 1045 (1956), Et$_3$N (1.5 mL, 10.5 mmol), phosgene (1.8 mL of a 1.93M solution in toluene, 3.5 mmol), and the compound resulting from Example 1B (0.60 g, 2.4 mmol) provided 0.68 g (71%) of the desired product which was converted to its HCl salt. m.p. 228°–230° C. $^1$H NMR (300 MHz, CD$_3$OD) of the free base δ 1.45–1.49 (m, 1H), 1.66–1.78 (m, 1H), 2.22 (t, 1H), 2.33 (dt, 1H), 2.50–2.68 (m, 3H), 2.77–2.86 (m, 2H), 3.24–3.51 (m, 3H), 3.77 (s, 3H), 4.20 (t, 2H), 6.71 (dd, 2H), 7.07 (t, 1H), 7.91 (d, 1H), 8.39 (d, 1H), 8.55 (s, 1H). MS (DCI/NH$_3$) m/e 393 (M+H)$^+$. Anal calcd for C$_{22}$H$_{24}$N$_4$O$_3$•2 HCl: C, 56.78; H, 5.63; N, 12.04. Found: C, 56.3 1; H, 5.63; N, 11.82.

EXAMPLE 25

3-[2-(cis-6-Methoxy-2,3,3a,4,5,9b-hexahydro-[1H]-benz[e]isoindol-1-yl)ethyl]-7-fluoro-quinazoline-2,4(1H,3H)-dione hydrchloride 2-Carboethoxy-5-fluoroaniline was treated with 0.33 equivalent triphosgene by the procedure described in Example 1C. The resulting isocyanate (0.46 g, 2.1 mmol) and the compound resulting from Example 1B (0.46 g, 1.9 mmol) were treated by the procedures described in Example 1C to yield the title compound (0.49 g, 60%) as a white solid. m.p. 236°–238° C. $^1$H NMR (300 MHz, CDCl$_3$) of the free base δ 7.95 (q, 1H), 7.1 (t, 1H), 6.72–6.8 (m, 2H), 6.67 (d, 1H), 6.55 (dd, 1H), 4.15–4.35 (m, 2H), 3.81 (s, 3H), 3.43–3.75 (m, 2H), 2.78–3.15 (m, 2H), 2.5–2.8 (m, 3H), 2.3–2.47 (m, 2H), 1.48–1.87 (m, 3H). MS (DCI/NH$_3$) m/e 410 (M+H)$^+$. Anal calcd for C$_{23}$H$_{24}$N$_3$O$_3$F.HCl.0.25 H$_2$O: C, 61.00; H, 5.62; N, 9.29. Found: C, 6133; H, 5.71; N, 9.33.

EXAMPLE 26

3-[2-(cis-6-Methoxy-2,3,3a,4,5,9b-hexahydro-[1H]-benz[e]isoindol-1-yl)ethyl]-1-methyl-quinazoline-2,4(1H,3H)-dione hydrochloride N-Methyl-2-carboethoxyaniline (5.0 g, 28 mmol) was treated with 2-chloroethylisocyanate (2.86 mL, 28 mmol) at reflux in toluene for 18 hours. The reaction was cooled to 25° C., and the crystalline product was collected by filtration to yield the intermediate 1-methyl-3-(2-chloroethyl)-quinazoline-2-4-dione. The intermediate quinazolinedione (0.53 g, 2.2 mmol) and cis-6-methoxy- 2,3,3a,4,5,9b-[1H]-benz[e]isoindole (0.38 g, 1.87 mmol) were combined in acetonitrile (3 mL) and diisopropylethylamine (0.8 mL) was added. The reaction mixture was heated at reflux for 18 hours. The resulting product was converted to its HCl salt and recrystallized from acetone:ether to yield the title compound (0.30 g, 40%) as a white solid. m.p. 215°–217° C. (dec). $^1$H NMR (300 MHz, CDCl$_3$) of the free base δ 8.2 (dd, 1H), 7.7 (dt, 1H), 7.1–7.32 (m, 3H), 6.75 (t, 2H), 4.48 (m, 3H), 4.1–4.3 (m, 2H), 3.81 (s, 3H), 3.68 (m, 1H), 3.6 (s, 3H), 3.35–3.5 (m, 2H), 2.87–4.3 (m, 2H), 2.72–2.87 (m, 2H), 2.52–2.65 (m, 1H), 1.88–2.0 (m, 1H), 1.55–1.7 (m, 1H). MS (DCI/NH$_3$) m/e 406 (M+H)$^+$. Anal calcd for C$_{24}$H$_{27}$N$_3$O$_3$.HCl. H$_2$O: C, 62.67; H, 6.57; N, 9.14. Found: C, 62.52; H, 6.51; N, 9.03.

EXAMPLE 27

3-[2-cis-6-Methoxy-2,3,3a,4,5,9b-hexahydro-[1H]-benz[e]isoindol-1-yl)ethyl]-pyrido[4,3-d]pyrimidine-2,4(1H,3H)-dione dihydrochloride Following the procedures described in Example 21, 4-amino-3-ethoxycarbonylpyridine (0.57 g, 3.4 mmol), prepared by the procedures described in *J. Org. Chem.*, 14: 97 (1949), Et$_3$N (0.85 mL, 6.1 mmol), phosgene (1.5 mL of 1.93M solution in toluene, 2.9 mmol), and the compound resulting from Example 1B (0.60 g, 2.4 mmol) provided 0.69 g (72%) of the desired product which was converted to its HCl salt. m.p. 229°–233° C. $^1$H NMR (300 MHz, CDCl$_3$) of the free base δ 1.49–1.62 (m, 1H), 1.75–1.87 (m, 1H), 2.38 (t, 2H), 2.50–2.77 (m, 3H), 2.88–2.98 (m, 1H), 3.09–3.20 (m, 1H), 3.47 (q, 1H), 3.69 (bt, 2H), 3.80 (s, 3H), 4.15–4.37 (m, 2H), 6.63 (d, 1H), 6.67 (d, 1H), 6.78 (d, 1H), 7.10 (t, 1H), 8.47 (d, 1H), 8.98 (s, 1H). MS (DCI/NH$_3$) m/e 393 (M+H)$^+$. Anal calcd for C$_{22}$H$_{24}$N$_4$O$_3$•2 HCl.1.5 H$_2$O: C, 53.66; H, 5.94; N, 11.38. Found: C, 53.83; H, 6.07; N, 11.31.

EXAMPLE 28

3-[2-(cis-6-Methoxy-2,3,3a,4,5,9b-hexahydro-[1H]-benz[e]isoindol-1-yl)ethyl]-1-methyl-1H-pyrazolo-[3,4-d]pyrimidine-4,6(5H,7H)-dione hydrochloride Ethyl-5-amino-1-methylpyrazole-4-carboxylate (0.40 g, 2.4 mmol) was dissolved in CH$_2$Cl$_2$ (10 mL) and triethylamine (0.68 mL, 4.89 mmol) and cooled to –78° C. To the solution was added 1.93M phosgene in toluene (1.23 mL, 2.4 mmol). After stirring at –78° C. for 1 hour and then 25° C. for 30 minutes, the compound resulting from Example 1B (0.53 g, 2.2 mmol) was added. After 2 hours, the intermediate unsymmetrical urea was isolated. The intermediate product (0.70 g) in ethanol (10 mL) was treated with 1.0M KOtBu in THF (2.0 mL) and the reaction was heated at 75° C. for 45 minutes. The reaction was quenched with 1.0N HCl to yield the title compound as its HCl salt. Recrystallization form methanol:ether yielded 0.420 g (45%) of a white solid. m.p. >250° C. (dec). $^1$H NMR (300 MHz, CD$_3$OD) δ 1.67 (m, 1H), 1.92 (m, 1H), 2.60 (m, 1H), 2.83 (m, 3H), 3.30 (m, 3H), 3.52 (t, 2H), 3.68 (br s, 1H), 3.81 (s, 3H), 3.82 (s, 3H), 4.32 (t, 2H), 6.79 (d, 1H), 6.82 (d, 1H), 7.18 (t, 1H), 7.85 (s, 1H). MS (DCI/NH$_3$) m/e 396 (M+H)$^+$. Anal calcd for C$_{21}$H$_{26}$ClN$_5$O$_3$•0.75 H$_2$O: C, 56.63; H, 6.22; N, 15.72. Found: C, 56.77; H, 5.86; N, 15.84.

EXAMPLE 29

3-[2-(cis-6-Methoxy-2,3,3,a,4,5,9b-hexahydro-[1H]-benz[e]isoindol-1-yl)ethyl]-6-methylthieno[2,3-d]-pyrimidine-2,4(1H,3H)-dione hydrochloride 2-Amino-3-carboethoxy-5-methylthiophene, prepared by the method of Gewald, et al., *Chem. Ber.*, 98: 94 (1966), was treated with 2-chloroethylisocyanate by the procedures described in *Eur. J. Med. Chem.*, 28: 499 (1993). The resulting urea (0.78 g, 2.7 mmol) and cis-6-methoxy-2,3,3a,4,5,9 b-hexahydro-[1H]-benz[e]isoindole (0.49 g, 2.42 mmol) were treated by the procedures described in Example 3 to yield 0.1410 g (15%) of the title compound as a white solid. m.p. >250° C. (dec). $^1$H NMR (300 MHz, DMSO-d$_6$) δ 1.60 (m, 1H), 1.80 (m, 1H), 2.40 (s, 3H), 2.50 (m, 1H), 2.70 (m, 2H), 3.00 (m, 2H), 3.42 (m, 3H), 3.79 (s, 3H), 4.11 (m, 1H), 4.18 (m, 3H), 6.76 (br d, 1H), 6.84 (d, 1H), 6.90 (s, 1H), 7.18 (t, 1H), 12.25 (br s, 1H). MS (DCI/NH$_3$) m/e 412 (M+H)$^+$. Anal calcd for C$_{22}$H$_{26}$ClN$_3$O$_3$S: C, 58.98; H, 5.85; N, 9.38. Found: C, 58.58; H, 5.84; N, 9.08.

EXAMPLE 30

3-[2-(cis-6-Methoxy-2,3,3a,4,5,9b-hexahydro-[1H]-benz[e]isoindol-1-yl)ethyl]1H-pyrrolo]2,3-d]pyrimidine-2,4(3H,7H)-dione fumarate 2-Amino-3,4-bis(ethoxycarbonyl)pyrrole, prepared by the method described in *J. Prakt. Chem.*, 314: 303 (1972), was reacted with 2-chloroethylisocyanate by the procedures described in *Eur. J. Med. Chem.* 28: 499 (1993). The resulting urea was reacted with cis-6-methoxy-2,3,3a,4,5, 9b-hexahydro-[1H]-benz[e]isoindole by the procedures described in Example 3. The urea ester intermediate (400 mg, 0.80 mmol) was treated with 5% KOH (50 mL) and heated at 110° C. for 1 hour. After cooling to room temperature the majority of the KOH was neutralized with concentrated HCl, followed by consumption of the remainder with solid NaHCO$_3$ resulting in the precipitation of the product at pH 12. The product was extracted into CH$_2$Cl$_2$, the organics dried (Na$_2$SO$_4$), filtered through celite and the solvent evaporated to give 196 mg of free base. The solid was dissolved in methanol and treated with a methanolic solution of fumaric acid (60 mg) to give 160 mg (39%) of the title compound as its fumarate salt. $^1$H NMR (300 MHz, CD$_3$OD) δ 1.62 (m, 1H), 1.90 (m, 1H), 2.58 (ddd, 1H), 2.78 (m, 1H), 2.82 (dt, 1H), 3.18 (m, 2H), 3.40 (t, 2H), 3.62 (dd, 1H), 3.81 (s, 3H), 3.86 (dd, 1H), 4.01 (dd, 1H), 4.33 (t, 2H), 6.42 (d, 1H), 6.64 (d, 1H), 6.65 (s, 2H), 6.77 (d, 1H), 6.81 (d, 1H), 7.15 (t, 1H). MS (DCI/NH$_3$) m/e 381 (M+H)$^+$. Anal calcd for C$_{25}$H$_{28}$N$_4$O$_7$•0.75 H$_2$O: C, 58.87; H, 5.83; N, 10.85. Found: C, 58.93; H, 5.73; N, 11.07.

EXAMPLE 31

3-[2-(cis-6-Methoxy-2,3,3a4,5,9b-hexahydro-[1H]-benz[e]isoindol-1-yl)ethyl]-7-phenylthieno[3,2-d]-pyrimidine-2,4(1H,3H)-dione methanesulfonate 2-Carboethoxy-3-amino-4-phenylthiophene, prepared by the method of Kirsch, et al., *J. Heterocyclic Chem.*, 19: 443 (1982), was treated with 0.33 equivalent triphosgene by the procedures described in Example 1C. The resulting isocyanate (0.90 g, 33 mmol) and the compound resulting from Example 1B (0.55 g, 2.2 mmol) were treated by the procedures described in Example 1C substituting methanesulfonic acid in the salt forming step, to yield the title compound (0.39 g, 38%) as a white solid. m.p. 268°–271° C. $^1$H NMR (300 MHz, DMSO-d$_6$) δ 1.6 (m, 2H), 1.8 (m, 2H), 2.65 (m, 3H), 3.0 (m, 2H), 3.35–3.55 (m, 3H), 3.75 (s, 3H), 4.0–4.25 (m, 2H), 6.75 (m, 1H), 6.85 (m, 1H), 7.18 (t, 1H), 7.45 (m, 3H), 8.15 (m, 2H), 10.35 (s, 1H). MS (DCI/NH$_3$) m/e 474 (M+H)$^+$. Anal calcd for C$_{27}$H$_{31}$N$_3$O$_6$S$_2$•0.25 H$_2$O: C, 58.57; H, 5.53; N, 7.32. Found: C, 58.62; H, 5.53; N, 6.99.

EXAMPLE 32

3-[2-(cis-6-Methoxy-2,3,3a,4,5,9b-hexahydro-[1H]-benz[e]isoindol-1-yl)ethyl]-6-phenylthieno-[3,2-d]pyrimidine-2,4(1H,3H)-dione hydrochloride 2-Carboethoxy-3-amino-5-phenylthiophene, prepared by the method described in *Synthesis*, 275 (1984), was treated with 0.33 equivalent triphosgene by the procedures described in Example 1C. The resulting isocyanate (0.54 g, 2.1 mmol) and the compound resulting from Example 1B (0.40 g, 1.6 mmol) were treated by the procedures described in Example 1C to yield the title compound (0.39 g, 38%) as a white solid. m.p. 229.5°–23 1° C. $^1$H NMR (300 MHz, DMSO-d$_6$) δ 1.6 (m, 2H), 1.8 (m, 2H), 2.65 (m, 3H), 3.0 (m, 2H), 3.35–3.55 (m, 3H), 3.75 (s, 3H), 4.0–4.25 (m, 2H), 6.8 (m, 2H), 7.18 (t, 1H), 7.3 (d, 1H), 7.5 (m, 3H), 7.8 (m, 2H), 10.35 (s, 1H). MS (DCI/NH$_3$) m/e 474 (M+H)$^+$. Anal calcd for C$_{27}$H$_{28}$ClN$_3$O$_3$S.0.5 H$_2$O: C, 62.48; H, 5.63; N, 8.10. Found: C, 62.29; H, 5.43; N, 8.10.

EXAMPLE 33

3-[2-(cis-6-Methoxy-2,3,3a,4,5,9b-hexahydro-[1H]-benz[e]isoindol-1-yl)ethyl]-6,7-dimethoxy-quinazoline-4(3H)-one dihydrochloride Ethyl 2-(N,N-dimethyl-N'-formamidinyl)-3,4-dimethoxybenzoate (1.68 g, 6.0 mmol), prepared from ethyl 6-amino-3,4-dimethoxybenzoate and using the procedures described by Gupton J. T., Miller J. F., Bryant R. D. Maloney P. R. and Foster B. S., *Tetrahedron*, 43(8): 1747–1752 (1987), and the compound resulting from Example 1C (0.59 g, 2.4 mmol) in 1,4-dioxane (20 mL) and p-toluenesulfonic acid monohydrate (0.05 g, 0.2 mmol) were refluxed for 4 hours and then concentrated to a crude oil. Trituration with MeOH afforded the product as a free base (0.66 g, 63%). A portion (0.32 g) was dissolved in methylene chloride followed and treated with HCl(g) in Et$_2$O to yield the title compound (0.37 g) as a white solid. mp 180°–185° C. (of a sample recrystallized from EtOH/Et$_2$O). $^1$H NMR (300 MHz, D$_2$O) δ 8.25 (s, 1H), 7.38 (br s, 1H), 7.25 (t, J=7.9 Hz, 1H), 7.05 (s, 1H), 6.94–6.89 (d, 1H), 6.91–6.86 (s, 1H), 4.72 (s, 3H), 4.44 (t, J=6.5 Hz, 2H), 3.97 (s, 3H), 3.92 (s, 3H), 3.83 (s, 3H), 3.70 (br s, 3H), 3.24–3.10 (br s, 1H), 2.85–2.74 (m, 2H), 2.61–2.53 (m, 1H), 1.97–1.90 (m, 1H), 1.66–1.62 (m, 1H), MS (DCI/NH$_3$) m/e 436 (M+H)$^+$. Anal calcd for C$_{25}$H$_{29}$N$_3$O$_4$•0.7 HCl•0.4 EtOH: C, 56.09 H, 6.22; N, 7.60. Found: C, 56.04; H, 6.35; N, 7.72.

EXAMPLE 34

3-[2-(cis-6-Methoxy-2,3,3a,4,5,9b-hexahydro-[1H]-benz[e]isoindol-1-yl)ethyl]-quinazoline-4(3H)-one dihydrochloride Methyl 2-(N,N-dimethyl-N'-formamidinyl) benzoate was prepared according to the method of Gupton J. T., Miller J. F., Bryant R. D. Maloney P. R., and Foster B. S., *Tetrahedron*, 43(8): 1747–1752 (1987). Methyl 2-(N,N-dimethyl-N'-formamidinyl) benzoate (1.7 g, 8.1 mmol) and the compound resulting from Example 1C (0.5 g, 2.0 mmol) were refluxed in a solution of 1,4-dioxane (25 mL) and p-toluenesulfonic acid monohydrate (0.04 g, 0.2 mmol) for 3 hours. The reaction mixture was concentrated to a crude oil which was triturated with hexane to give a crude solid. The solid was collected by filtration and washed with EtOAc to give a white solid. The free base was dissolved in methylene chloride and treated with an ethereal solution of HCl to yield the title compound (0.40 g, 45%) as a white solid. m.p. >200° C. (on a sample recrystallized from EtOH/Et$_2$O). $^1$H NMR (300 MHz, D$_2$O) δ 8.38 (s, 1H), 8.23 (br d, 1H), 7.94 (t, J=7.6 Hz, 1H), 7.76–7.73 (d, 1H), 7.67 (t, J=73 Hz, 1H), 7.26 (t, J=7.9 Hz, 1H), 6.95–6.90 (d, 1H), 6.93–6.88 (d, 1H), 4.66–4.56 (m, 3H), 4.48 (t, J=7.5 Hz, 2H), 3.84 (s, 3H), 3.72–3.60 (m, 3H), 3.18 (br s, 1H), 2.82 (br s, 2H), 2.62–2.53 (m, 1H), 1.97–1.90 (m, 1H), 1.65 (br s, 1H). MS (DCI/NH$_3$) m/e 876 (M+H)$^+$. Anal calcd for C$_{23}$H$_{27}$Cl$_2$N$_3$O$_2$•0.3 HCl•0.2 EtOH: C, 59.98 H, 6.13; N, 8.96. Found: C, 59.88; H, 6.17; N, 8.95.

EXAMPLE 35

3-[2-(cis-6-Hydroxy-2,3,3a,4,5,9b-hexahydro-[1H]-benz[e]isoindol-1-yl)ethyl]-thieno[23-d]pyrimidine-2,4(1H,3H)-dione hydrobromide To a suspension of the compound resulting from Example 3 (100 mg, 0.23 mmol, 1.0 equiv) in 3 mL of methylene chloride cooled to −78° C. was added 0.46 mL of 1M BBr$_3$ in methylene chloride (0.46 mmol, 2.0 equiv). The reaction was then warmed to room temperature and stirred for 5 hours. The oily suspension was then cooled to −78° C. and quenched with 20 mL of dry methanol. The reaction solution was then evaporated to a tan solid which was crystallized from methanolmethylene chloride to furnish the title compound as a white powder (95 mg, 93%). m.p. >200° C. $^1$H NMR (CD$_3$OD, 300 MHz) δ 1.60 (1H, m), 1.90 (1H, m), 2.57 (1H, m), 2.80 (2H, m), 3.30 (1H, m), 3.35 (1H, m), 3.55 (2H, t, J=6.0 Hz), 3.62 (1H, m), 3.90 (2H, m), 4.35 (2H, t, J=6.0 Hz), 4.95 (1H, m) , 6.65 (2 H, m), 7.0 (1H, t, J=7.5 Hz), 7.06 (1H, d, J=7.5 Hz), 7.25 (1H, d, J=7.5 Hz). MS (DCI/NH$_3$) m/e 384 (M+H)$^+$. IR (KBr): 3400, 2720, 2650, 1720, 1640 cm$^{-1}$. Anal calcd for C$_{20}$H$_{22}$N$_3$O$_3$SBr: C, 51.73; H, 4.78; N, 9.05. Found: C, 51.39; H, 4.76: N 8.78.

EXAMPLE 36

3-[2-((3aR,9bR)-cis-6-Methoxy-2,3,3a,4,5,9b-hexahydro-[1H]-benz[e]isoindol-1-yl)ethyl]-quinazoline-2(1H)-one hydrochloride

EXAMPLE 36A

2-[2-((3aR,9bR)-cis-6-Methoxy-2,3,3a,4,5,9b-hexahydro-[1H]-benz[e]isoindol-1-yl)ethyl]aminomethyl-aniline Using the procedure described by Langley D. R., Thurston. D. E., *J. Org. Chem.* 52 (1): 91–97 (1987), 2-nitrobenzyl bromide and the compound resulting from Example 13J were reacted with stannous chloride dihydrate in methanol to afford the title compound.

EXAMPLE 36B

3-[2-((3aR,9bR)-cis-6-Methoxy-2,3,3a,4,5,9b-hexahydro-[1H]-benz[e]isoindol-1-yl)ethyl]-quinazoline-2(1H)-one hydrochloride A solution of the compound resulting from Example 36A (136 mg, 0.387 mmol) in 4 mL of dry tetrahydrofuran was cooled and a solution of 75.3 mg (0.464 mmol) of N,N'-carbonyldiimidazole in 2 mL of dry tetrahydrofuran was added rapidly with stirring. The cooling bath was removed and stirring was continued for 3 hours. The solvent was evaporated to give the crude product. Chromatography on silica gel eluting with 3% MeOH in CHCl$_3$ afforded the product as a free base. The free base was dissolved in methylene chloride and treated with HCl(g) in Et$_2$O as to yield the title compound (45 mg) as a white solid. m.p. 145°–147° C. (on a sample recrystallized from EtOH/Et$_2$O). $^1$H NMR (300 MHz, CD$_3$OD) δ 1.30 (m, 1H), 1.55–1.70 (m, 3H), 2.20 (m, 2H), 2.52–2.65 (m, 4H), 2.72 (m, 2H), 3.25 (m, 1H), 3.35 (s, 2H), 3.42 (m, 1H), 3.82 (s, 3H), 6.70 (m, 4H), 7.20 (m, 3H). MS (DCI/NH$_3$) m/e 378 (M+H)$^+$. Anal. calcd for C$_{23}$H$_{28}$N$_3$O$_2$Cl•0.9 HCl: C, 61.83; H, 6.52; N, 9.41. Found: C, 61.91; H, 6.46; N, 9.29.

EXAMPLE 37

3-[2-((3aR,9bR)-cis-6-Methoxy-2,3,3a,4,5,9b-hexahydro-[1H-benz[e]isoindol-1-yl)ethyl]-6,7-methylenedioxyquinazoline-2,4(1H,3H)-dione hydrochloride Following the procedure described for Example 21, 6-amino-1,3-benzodioxole- 5-carboxylic acid ethyl ester (0.51 g, 2.4 mmol), prepared in analogy to the procedure described in *J. Indian Chem. Soc.*, 64(6), 373–5 (1987), Et$_3$N (0.74 mL, 5.3 mmol), phosgene (1.3 mL 1.93M solution in toluene, 2.4 mmol), and the compound resulting from Example 13J (0.50 g, 2.0 mmol) were reacted to give 0.82 g (93%) of the desired product as its HCl salt. m.p. 257°–258° C. $^1$H NMR (300 MHz, CDCl$_3$) of the free base δ 1.46–1.61 (m, 1H), 1.71–1.86 (m, 1H), 2.22–2.36 (m, 2H), 2.50–2.75 (m, 3H), 2.80–2.92 (m, 1H), 3.03–3.13 (m, 1H), 3.40–3.52 (m, 1H), 3.63–3.76 (m, 2H), 3.81 (s, 3H), 4.15–4.35 (m, 2H), 6.00 (s, 2H), 6.23 (s, 1H), 6.65 (d, 1H), 6.76 (d, 1H), 7.08 (t, 1H), 7.23 (s, 1H). MS (DCI/NH$_3$) m/e 436 (M+H)$^+$. Anal calcd for C$_{24}$H$_{25}$N$_3$O$_5$.HCl): C, 61.08; H, 5.55; N, 8.90. Found: C, 60.81; H, 5.51; N, 8.78.

EXAMPLE 38

3-[2-((3aR,9bR)-cis-6-Methoxy-2,3,3a,4,5,9b-hexahydro-[1H]-benz[e]isoindol-1-yl)ethyl]-6,7-ethylenedioxyquinazoline-2,4(1H,3H)-dione hydrochloride Following the procedure described for Example 21, 7-amino-2,3-dihydro- 1,4-benzodioxane-6-carboxylic acid ethyl ester (0.55 g, 2.4 mmol), prepared in analogy to the procedure described in U.S. Pat. No. 4,011,323 which is incorporated herein by reference, Et$_3$N (0.74 mL, 53 mmol), phosgene (1.3 mL 1.93M solution in toluene, 2.4 mmol), and the compound resulting from Example 13J (0.50 g, 2.0 mmol) were reacted to give 0.91 g (99%) of the desired product as its HCl salt. m.p. 212°–214° C. $^1$H NMR (300 MHz, CDCl$_3$) of the free base δ 1.48–1.65 (m, 1H), 1.72–1.87 (m, 1H), 2.20–2.33 (m, 2H), 2.52–2.71 (m, 3H), 2.86–3.00 (m, 1H), 3.08–3.21 (m, 1H), 3.42–3.57 (m, 1H), 3.73–3.90 (m, 2H), 3.81 (s, 3H), 4.16–4.42 (m, 6H), 6.18 (s, 1H), 6.66 (d, 1H), 6.79 (d, 1H), 7.09 (t, 1H), 7.28 (s, 1H). MS (DCI/NH$_3$) m/e 450 (M+H)$^+$. Anal calcd for C$_{25}$H$_{27}$N$_3$O$_5$.HCl.0.5 H$_2$O: C, 60.66; H, 5.91; N, 8.49. Found: C, 60.69; H, 5.73; N, 8.37.

EXAMPLE 39

3-[2-((3aR,9bR)-cis-6-Methoxy-2,3,3a,4,5,9b-hexahydro-[1H]-benz[e]isoindol-1-yl)ethyl]-6,7-dimethoxyquinazoline-2,4(1H,3H)-dione hydrochloride The compound resulting from Example 13J (2.44, 0.6 g) was reacted with 0.7 g of the isocyanate derived from methyl 2-amino-4,5-dimethoxy-benzoate as in Example 10 to yield 0.6 g (54%). of the title compound. $^1$H NMR (300 MHz, DMSO-d$_6$) δ 7.36 (s, 1H), 7.18 (t, 1H), 6.81 (s, 1H), 6.85 (d, 1H), 6.75 (d, 1H), 4.2–4.32 (m, 3H), 3.9–4.1 (m, 1H), 3.88 (s, 3H), 3.84 (s, 3H), 3.8 (s, 3H), 3.65 (m, 1H), 3.42 (m, 3H), 2.92–3.6 (m, 2H), 2.6–2.85 (m, 2H), 1.73–1.88 (m, 1H), 1.52–1.68 (m, 1H). Anal calcd for C$_{25}$H$_{29}$N$_3$O$_5$.HCl.H$_2$O: C, 59.34; H, 6.37; N, 8.30. Found: C, 59.73; H, 6,20; N, 8.23.

EXAMPLE 40

3-[2-((3aR,9bR)-cis-6-Methoxy-2,3,3a,4,5,9b-hexahydro-[1H]-benz[e]isoindol-1-yl)ethyl]1-methyl6,7-dimethoxyquinazoline-2,4(1H,3H)-dione hydrochloride The compound resulting from Example 13J (203 mg, 1 mmol) and 0.3 g (1.05 mmol) 6,7-dimethohy-1-methylquinazoline-2,4-dione were reacted as described in Example 26 to yield 0.235 g (64%) of the title compound as a white solid. m.p. 188°–190° C. $^1$H NMR (300 MHz, CDCl$_3$) of the free base δ 7.61 (s, 1H), 7.1 (t, 1H), 6.78 (d, 1H), 6.66 (d, 1H), 6.58 (s, 1H), 4.25 (t, 2H), 4.02 (s, 3H), 3.95 (s, 3H), 3.81 (s, 3H), 3.6 (s, 3H), 3.42 (m, 3H), 2.48–2.87 (m, 5H), 2.28 (m, 2H), 1.75 (m, 1H), 1.52 (m, 1H). Anal calcd for C$_{25}$H$_{29}$N$_3$O$_5$.HCl•H$_2$O: C, 60.05; H, 6.59; N, 8.08. Found: C, 59.51; H, 6.36; N, 7.93.

EXAMPLE 41

3-[2-(cis-6-Methoxy-2,3,3a,4,5,9b-hexahydro-[1H]-benz[e]isoindol-1-yl)ethyl]-6-methoxy-thieno-[3,2-d]pyrimidine-2,4(1H,3)-dione hydrchloride

EXAMPLE 41A

5-Amino-4-carboethoxy-2-methoxythiophene

To methanol (404 μL, 10 mmol) in THF (10 mL) at 0° C. under nitrogen was added 2.5M n-BuLi (4.0 mL, 10 mmol). After stirring 20 minutes, CS$_2$ (600 μL, 10 mmol) was added and stirring was continued for 4 hours. The reaction was then cooled to 0° C. followed by the addition of MeI (620 μL, 10 mmol) whereupon the reaction was stirred for 4 hours at 0° C. then at ambient temperature overnight. In a separate flask the anion of acetonitrile was prepared by the dropwise addition of acetonitrile (520 μL, 10 mmol) to a solution of LDA (10 mmol) in THF at −78° C. followed by stirring for 30 minutes at that temperature. To the acetonitrile anion was added the solution of the xanthate prepared above. The reaction was stirred for 1 hour at −78° C. then 1 hour at 0° C. The reaction was then cooled to −78° C., treated with ethyl bromoacetate (1.1 mL, 10 mmol), warmed to reflux, treated with 1.0M lithium bistrimethylsilylamide (1 mL) and heated at reflux for 1.5 hours. After cooling the reaction, it was partitioned between saturated NaHCO$_3$ solution and methylene chloride. The organic layer was then dried with sodium sulfate, filtered, concentrated in vacuo and flash chromatographed eluting with 4:1 hexane-ethyl acetate to give 343 mg (17% yield) of the title compound.

EXAMPLE 41B

3-[2-(cis-6-Methoxy-2,3,3a,4,5,9b-hexahydro-[1H]-benz[e]isoindol-1-yl)ethyl]-6-methoxy-thieno-[3,2-d]pyrimidine-2,4(1H,3H)-dione hydrochloride The compound resulting from Example 41A (303 mg) was reacted according to the standard procedure for in situ isocyanate formation with the compound resulting from Example 13J (0.375 g, 1.52 mmol) to give 240 mg (38%) of product as the free base which was converted to the fumarate salt giving 149 mg (18%). m.p. 217° C. $^1$H NMR (300 MHz, DMSO-d$_6$) δ 1.45 (1H, m), 1.65 (1H, m), 2.23 (1H, m), 2.32 (1H, m), 2.44 (2H, m), 2.58 (1H, m), 2.66 (2H, m), 3.30 (3H, m), 3.75 (3H, s), 3.95 (2H, t), 3.99 (3H, s), 6.10 (1H, s), 6.59 (2H, s), 6.7 (1H, d), 6.75 (1H, d), 7.09 (1H, t), 11.76 (1H, br s). Anal calcd for C$_{26}$H$_{29}$N$_3$O$_8$S: C, 57.45; H, 5.38; N, 7.73. Found: C, 57.17; H, 5.23; N, 7.63.

EXAMPLE 42

3-[2-((3aR,9bR)-cis-6-Methoxy-2,3,3a,4,5,9b-hexahydro-[1H]-benz[e]isoindol-1-yl)ethyl]6,7-dimethoxy-quinazoline-4(3H)-one dihydrochloride Ethyl 2-(N,N-dimethyl-N'-formamidinyl)-3,4-dimethoxybenzoate (5.67 g, 20.3 mmol), prepared according to the method described by Cupton J. T., Miller J. F., Bryant R. D. Maloney P. R., Foster B. S. in Tetrahedron 43(8) 1747–1752 (1987) from ethyl 6-amino-3,4-dimethoxybenzoate, and The compound resulting from Example 13J (2.0 g, 8.1 mmol) refluxing in a solution of 1,4-dioxane (30 mL) and p-toluenesulfonic acid monohydrate (0.15 g, 0.8 mmol) for 4 hours. The reaction mixture was concentrated to a crude oil which was recrystallized from MeOH to give the product as the free base. The free base was dissolved in methylene chloride and treated with HCl in Et$_2$O to yield the title compound (3.59 g, 87%) as a white solid. m.p. 180°–185° C. (on a sample recrystallized from EtOH-Et$_2$O). $^1$H NMR (300 MHz, D$_2$O) δ 8.31 (s, 1H), 7.42 (br s, 1H), 7.24 (t, J=7.9 Hz, 1H), 7.08 (s, 1H), 6.94–6.89 (d, 1H), 6.91–6.87 (d, 1H), 4.72 (s, 3H), 4.45 (t, J=6.5 Hz, 2H), 3.98 (s, 3H), 3.93 (s, 3H), 3.83 (s, 3H), 3.70 (br s, 3H), 3.22–3.10 (br s, 1H), 2.85–2.74 (m, 2H), 2.62–2.51 (m, 1H), 1.97–1.90 (m, 1H), 1.66–1.62 (m, 1H). MS (DCI/NH$_3$) m/e 436 (M+H)$^+$. [α]$_D$=+27.4° (c=0.53, CH$_3$OH). Anal. calcd for C$_{25}$C$_{29}$N$_3$O$_4$.0.1 HCl.0.8 H$_2$O: C, 57.03; H, 6.26; N, 7.98. Found: C, 57.10; H, 6.25; N, 7.93.

EXAMPLE 43

3-[2-((3aR,9bR)-cis-6-Methoxy-2,3,3a,4,5,9b-hexahydro-[1H]-benz[e]isoindol-1-yl)ethyl]-thieno-[2,3-d]pyrimidine-4(3H)-one hydrochloride 3-[(N,N-Dimethyl-N'-formamidinyl)]carboxyethylthiophene was prepared from 3-(2-amino)-carboxyethylthiophene by the method described in Cupton J. T., Miller J. F., Bryant R. D. Maloney P. R., Foster B. S., Tetrahedron 43(8) 1747–1752(1987).

3-[(N,N-Dimethyl-N'-formamidinyl)]-carboxyethylthiophene (0.92 g, 4.1 mmol) and the compound resulting from Example 13J (0.40 g, 1.6 mmol) were heated under reflux in a solution of 1,4-dioxane (6.0 mL) and p-toluenesulfonic acid monohydrate (0.03 g, 0.2 mmol) for 3 hours. The reaction mixture was concentrated and then purified by flash column chromatography on silica gel eluting with EtOAc to give free base as an oil. The free, base was dissolved in methylene chloride and treated with HCl(g) in Et$_2$O to yield the title compound (0.16 g, 22%) as a solid. m.p. 171°–175° C. (on a sample recrystallized from MeOH-Et$_2$O). $^1$H NMR (300 MHz, DMSO-d$_6$) δ 8.50 (br s, 1H), 7.64–7.62 (d, 1H), 7.44–7.42 (d, 1H), 7.16 (t, J=9.5 Hz), 6.84–6.81 (d, 1H), 6.78–6.76 (d, 1H), 4.45–4.30 (br s, 2H), 4.13 (br s, 1H), 4.00 (br s, 1H), 3.77 (s, 3H), 3.70–3.45 (m, 3H), 3.01 (br s, 1H), 2.72–2.67 (m, 2H), 2.50–2.38 (m, 2H), 1.76 (br s, 1H), 1.60 (br s, 1H). MS (DCI/NH$_3$) m/e 882 (M+H)$^+$. [α]$_D$=+19.1° (c=0.35, CH$_3$OH). Anal. calcd for C$_{21}$H$_{23}$N$_3$O$_2$S.0.1 H$_2$O: C, 55.28; H, 6.56; N, 9.21. Found: C, 55.33; H, 5.72; N, 9.02.

EXAMPLE 44

3-[2-((3aR,9bR)-cis-6-Methoxy-2,3,3a,4,5,9b-hexahydro-[1H]-benz[e]isoindol-1-yl)ethyl]-quinazoline-2(1H)-one hydrochloride 2-[2-((3aR,9bR)-cis-6-Methoxy-2,3,3a,4,5,9b-hexahydro.[1H]-benz[e]isoindol-1-yl)ethyl]aminomethyl aniline was prepared from 2-nitrobenzyl bromide and the compound resulting from Example 13J using stannous chloride dihydrate in methanol by the procedure of Langley D. R. and Thurston. D. E, J. Org. Chem. 52 (1), 91–97 (1987).

The above prepared compound (136 mg, 0.387 mmol) in 4 mL of dry tetrahydrofuran was cooled in an ice bath, and a solution of 75.3 mg (0.464 mmol) of N,N'-carbonyldiimidazole in 2 mL of dry tetrahydrofuran was added rapidly with stirring. The cooling bath was removed and stirring was continued for 3 hours. The solvent was evaporated to give the crude product. Chromatography on silca gel eluting with 3% MeOH in CHCl$_3$ afforded the product as a free base. The free base was dissolved in methylene chloride and treated with a solution of HCl(g) dissolved in Et$_2$O to give the title compound (45 mg) as a white solid. m.p. 145°–147° C. (on a sample recrystallized from EtOH-Et$_2$O). $^1$H NMR (300 MHz, CD$_3$OD) δ 1.30 (m,1H), 1.55–1.70 (m, 3H), 2.20(m, 2H), 2.52–2.65 (m, 4H), 2.72 (m, 2H), 3.25 (m, 1H), 3.35 (s, 2H), 3.42 (m, 1H), 3.82 (s, 3H), 6.70 (m, 4H), 7.20 (m, 3H). MS (DCI/NH$_3$) m/e 378 (M+H)$^+$. Anal. calcd for C$_{23}$H$_{27}$N$_3$O$_2$.0.90 HCl: C, 61.83; H, 6.52; N, 9.41. Found: C, 61.91; H, 6.46; N, 9.29.

EXAMPLE 45

3-[2-(cis-6-Methoxy-2,3,3a,4,5,9b-hexahydro-[1H]-benz[e]isoindol-1-yl)ethyl]-1,2-dihydro-quinazoline-4(3H)-one dihydrochloride The compound resulting from Example 34 (0.15 g, 0.3 mmol) in methanol (25 mL) was hydrogenated at 4 atmosphere of H$_2$ at room temperature using a 10% Pd/C catalyst (dry, 0.02 g) for 17 hours. The catalyst was removed by filtrated and the filtrate concentrated. The residue obtained was dissolved in water, basified to pH 13 with potassium carbonate and extracted with Et$_2$O and EtOAc. The combined organic extracts were dried over anhydrous Na$_2$SO$_4$ and concentrated to give, after flash column chromatography eluting with 10:90 EtOH-EtOAc, the free base as a white solid. The free base was dissolved in methylene chloride treated with a solution of HCl(g) dissolved in Et$_2$O to give the title compound (0.05 g, 37%) as a white solid. m.p. 130° C. (dec). $^1$H NMR (300 MHz, CD$_3$OD) δ 7.81 (dd, J=1.5 Hz, 1H), 7.79–7.78 (dd, J=1.3 Hz, 1H), 7.3–7.31 (m, 1H), 7.16 (t, J=8.1 Hz, 1H), 6.86–6.77 (m, 4H), 4.69 (s, 2H), 4.29–4.13 (m, 2H), 3.88–3.72 (m, 2H), 3.81 (s, 3H), 3.64–3.45 (m, 4H), 3.14–3.03 (m, 2H), 2.87–2.78 (m, 2H), 2.58–2.56 (m, 1H), 1.94–1.89 (m, 1H), 1.69–1.65 (m, 1H). MS (DCI/NH$_3$) m/e 378 (M+H)$^+$. Anal. calcd for C$_{23}$H$_{27}$N$_3$O$_2$•0.1 HCl.0.8 H$_2$O: C, 58.97; H, 6.60; N, 8.97. Found: C, 59.06; H, 6.65; N, 8.59.

EXAMPLE 46–81

The following compounds can be prepared by the procedures described in the preceding examples and schemes.

| Example | Name |
|---|---|
| 46 | 2-[2-(cis-6-Methoxy-2,3,3a,4,5,9b-hexahydro-[1H]-benz[e]isoindol-1-yl)ethyl]-1,2,3,4-tetrahydroisoquinolin-1,3-dione |
| 47 | 2-[2-(cis-6-Methoxy-2,3,3a,4,5,9b-hexahydro-[1H]-benz[e]isoindol-1-yl)ethyl]-6,7-dimethoxy- 1,2,3,4-tetrahydroisoquinoline |
| 48 | 3-[2-(cis-6-Methoxy-2,3,3a,4,5,9b-hexahydro-[1H]-benz[e]isoindol-1-yl)ethyl]-2,4-pteridinedione |
| 49 | 3-[2-(cis-6-Methoxy-2,3,3a,4,5,9b-hexahydro-[1H]-benz[e]isoindol-1-yl)ethyl]-7-(3,4-dimethoxyphenyl)-thieno[3,2-d]pyrimidine-2,4(1H,3H)-dione |
| 50 | 3-[2-(cis-6-Methoxy-2,3,3a,4,5,9b-hexahydro-[1H]-benz[e]isoindol-1-yl)ethyl]-1-methyl-thieno[2,3-d]pyrimidine-2,4(1H,3H)-dione |
| 51 | 3-[2-(cis-6-Methoxy-2,3,3a,4,5,9b-hexahydro-[1H]-benz[e]isoindol-1-yl)ethyl]-6-chloro-thieno[2,3-d]pyrimidine-2,4(1H,3H)-dione |
| 52 | 3-[2-(cis-6-Methoxy-2,3,3a,4,5,9b-hexahydro-[1H]-benz[e]isoindol-1-yl)ethyl]-1-methyl-dimethylaminocarbonyl-thieno[2,3-d]pyrimidine-2,4(1H,3H)-dione |
| 53 | 3-[2-(cis-6-Methoxy-2,3,3a,4,5,9b-hexahydro-[1H]-benz[e]isoindol-1-yl)ethyl]-oxazolo[5,4-d]pyrimidine-5,7(4H,6H)-dione |
| 54 | 3-[2-(cis-6-Methoxy-2,3,3a,4,5,9b-hexahydro-[1H]-benz[e]isoindol-1-yl)ethyl]-7-amino-oxazolo[5,4-d]pyrimidin-5(6H)-one |
| 55 | 1-[2-(cis-6-Methoxy-2,3,3a,4,5,9b-hexahydro-[1H]-benz[e]isoindol-1-yl)ethyl]-3,9-dimethyl-[1H]-purine-2,6-dione |
| 56 | 1-[2-(cis-6-Methoxy-2,3,3a,4,5,9b-hexahydro-[1H]-benz[e]isoindol-1-yl)ethyl]-3,7-dimethyl-[7H]-imidazo[4,5-d]pyrimidin-2,6-dione |
| 57 | 3-[4-(cis-9-Methoxy-2,3,3a,4,5,9b-hexahydro-[1H]-benz[e]isoindol-1-yl)butyl]-6,7-dimethoxy-quinazoline-2,4(1H,3H)-dione |
| 58 | 3-[2-(cis-6-Methoxy-2,3,3a,4,5,9b-hexahydro-[1H]-benz[e]isoindol-1-yl)ethyl]-7,8-dimethoxy-quinazoline-2,4(1H,3H)-dione |
| 59 | 3-[2-(cis-6-Methoxy-2,3,3a,4,5,9b-hexahydro-[1H]-benz[e]isoindol-1-yl)ethyl]-7-methoxy-quinazoline-2,4(1H,3H)-dione |
| 60 | 3-[2-(cis-6-Methoxy-2,3,3a,4,5,9b-hexahydro-[1H]-benz[e]isoindol-1-yl)ethyl]-7,8-dimethyl-quinazoline-2,4(1H,3H)-dione |
| 61 | 3-[2-(cis-6-Methoxy-2,3,3a,4,5,9b-hexahydro-[1H]-benz[e]isoindol-1-yl)ethyl]-7-methylsulfonylamino-quinazoline-2,4(1H,3H)-dione |
| 62 | 3-[2-(cis-6-Methoxy-2,3,3a,4,5,9b-hexahydro-[1H]-benz[e]isoindol-1-yl)ethyl]-7,8-ethylenedioxy-quinazoline-2,4(1H,3H)-dione |
| 63 | 3-[2-(cis-6-Hydroxy-2,3,3a,4,5,9b-hexahydro-[1H]-benz[e]isoindol-1-yl)ethyl]-6,7-dimethoxy-quinazoline-2,4(1H,3H)-dione |
| 64 | 2-[2-(cis-6-Methoxy-2,3,3a,4,5,9b-hexahydro-[1H]-benz[e]isoindol-1-yl)ethyl]-4-amino-6,7-dimethoxy-quinazoline |
| 65 | 3-[2-(cis-6-Methoxy-2,3,3a,4,5,9b-hexahydro-[1H]-benz[e]isoindol-1-yl)ethyl]-6-chloro-7-methoxy-quinazoline-2,4(1H,3H)-dione |
| 66 | 3-[2-(cis-6-Methoxy-2,3,3a,4,5,9b-hexahydro-[1H]-benz[e]isoindol-1-yl)ethyl]-6-methoxy-7-chloro-quinazoline-2,4(1H,3H)-dione |
| 67 | 3-[2-(cis-6-Methoxy-2,3,3a,4,5,9b-hexahydro-[1H]-benz[e]isoindol-1-yl)ethyl]-7-dimethylaminocarbonyl-quinazoline-2,4(1H,3H)-dione |
| 68 | 3-[2-(cis-6-Methoxy-2,3,3a,4,5,9b-hexahydro-[1H]-benz[e]isoindol-1-yl)ethyl]-7-cyano-quinazoline-2,4(1H,3H)-dione |
| 69 | 3-[2-(trans-9-Methoxy-2,3,3a,4,5,9b-hexahydro-[1H]-benz[e]isoindol-1-yl)ethyl]-[1H,3H]-quinazoline-2,4(1H,3H)-dione |
| 70 | 3-[2-(trans-6-Methoxy-2,3,3a,4,5,9b-hexahydro-[1H]-benz[e]isoindol-1-yl)ethyl]-thieno[3,2-d]pyrimidine-2,4(1H,3H)-dione |
| 71 | 3-[2-(trans-6-Methoxy-2,3,3a,4,5,9b-hexahydro-[1H]-benz[e]isoindol-1-yl)ethyl]-8-methoxy-quinazoline-2,4(1H,3H)-dione |
| 72 | 3-[2-(trans-6-Methoxy-2,3,3a,4,5,9b-hexahydro-[1H]-benz[e]isoindol-1-yl)ethyl]-6,7-dimethoxy-quinazoline-2,4(1H,3H)-dione |
| 73 | 3-[2-(trans-6-Methoxy-2,3,3a,4,5,9b-hexahydro-[1H]-benz[e]isoindol-1-yl)ethyl]-7-chloro-quinazoline-2,4(1H,3H)-dione |
| 74 | 3-[2-(trans-6-Methoxy-2,3,3a,4,5,9b-hexahydro-[1H]-benz[e]isoindol-1-yl)ethyl]-7-carbomethoxy-quinazoline-2,4(1H,3H)-dione |
| 75 | 3-[2-(trans-6-Methoxy-2,3,3a,4,5,9b-hexahydro-[1H]-benz[e]isoindol-1-yl)ethyl]-6,7,8-trimethoxy-quinazoline-2,4(1H,3H)-dione |
| 76 | 3-[2-(trans-6-Methoxy-2,3,3a,4,5,9b-hexahydro-[1H]-benz[e]isoindol-1-yl)ethyl]-1-methyl-quinazoline-2,4(1H,3H)-dione |
| 77 | 3-[2-(trans-6-Methoxy-2,3,3a,4,5,9b-hexahydro-[1H]-benz[e]isoindol-1-yl)ethyl]-6,7-dimethoxy-quinazoline-4(3H)-one |
| 78 | 3-[2-(trans-6-Methoxy-2,3,3a,4,5,9b-hexahydro-[1H]-benz[e]isoindol-1-yl)ethyl]-6,7-methylenedioxyquinazoline-2,4(1H,3H)-diorie |
| 79 | 3-[2-(trans-6-Methoxy-2,3,3a,4,5,9b-hexahydro-[1H]-benz[e]isoindol-1-yl)ethyl]-6,7-ethylenedioxyquinazoline-2,4(1H,3H)-dione |
| 80 | 3-[2-(trans-6-Methoxy-2,3,3a,4,5,9b-hexahydro-[1H]-benz[e]isoindol-1-yl)ethyl]-1-methyl-6,7-dimethoxyquinazoline-2,4(1H,3H)-dione |
| 81 | 3-[2-(trans-6-Methoxy-2,3,3a,4,5,9b-hexahydro-[1H]-benz[e]isoindol-1-yl)ethyl]-6-methoxy-thieno[3,2-d]pyrimidine-2,4(1H,3H)-dione |

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound of the formula:

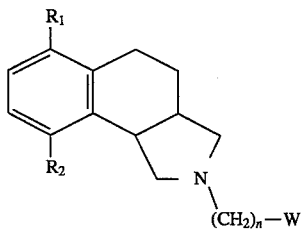

or a pharmaceutically acceptable salt thereof wherein n is an integer from 2 to 6;

R$_1$ and R$_2$ are independently selected from the group consisting of
hydrogen,
alkyl of one to six carbon atom,
alkoxy of one to six carbon atoms,
hydroxy,
halo,
carboxy, and
alkoxycarbonyl of two to eight carbon atoms;

W is selected from the group consisting of

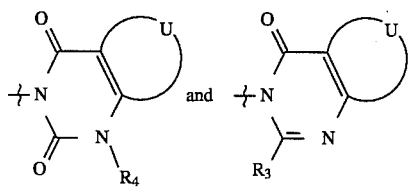

wherein R$_3$ is selected from the group consisting of
hydrogen,
alkyl of one to six carbon atoms,
unsubstituted phenyl and
phenyl substituted with alkyl of one to six carbon atoms, and R$_4$ is hydrogen or alkyl of one to six carbon atoms; and U, taken together with the carbon atoms to which it is attached forms a ring selected from the group consisting of (a) an unsubstituted or substituted five membered ring having four carbon atoms, two double bonds and one heteroatom selected from the group consisting of —N(R$_5$)—, —O— and —S— wherein R$_5$ is hydrogen or alkyl of one to six carbon atoms and the ring substituent is selected from the group consisting of alkyl of one to six carbon atoms, phenyl, halo, cyano, nitro, carboxy, alkoxycarbonyl of two to eight carbon atoms and alkoxy of one to six carbon atoms;

(b) an unsubstituted or substituted five membered ring having three carbon atoms, two double bonds and two heteroatoms selected from the group consisting of two nitrogen atoms, one oxygen atom and one nitrogen atom, and one sulfur atom and one nitrogen atom wherein the ring substituent is selected from the group consisting of alkyl of one to six carbon atoms, phenyl, halo, cyano, nitro, carboxy, alkoxy-carbony of two to eight carbon atoms and alkoxy of one to six carbon atoms;

(c) a benzene ring which is unsubstituted or substituted with alkyl of one to six carbon atoms, phenyl, halo, cyano, nitro, carboxy, alkoxycarbonyl of two to eight carbon atoms and alkoxy of one to six carbon atoms methylenedioxy and ethylenedioxy; and (d) an unsubstituted or substituted six membered ring having one to three double bonds and one or two nitrogen atoms, wherein the ring substituents are selected from the group consisting of alkyl of one to six carbon atoms, phenyl, halo, cyano, nitro, carboxy, alkoxycarbonyl of two to eight carbon atoms and alkoxy of one to six carbon atoms.

2. A compound according to claim 1 having the formula:

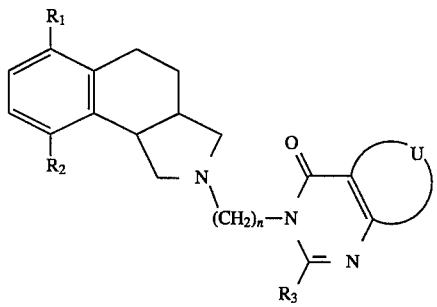

or a pharmaceutically acceptable salt thereof.

3. A compound according to claim 1 having the formula:

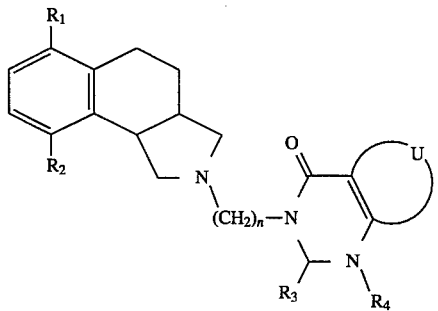

or a pharmaceutically acceptable salt thereof.

4. A compound according to claim 1 wherein W is selected from the group consisting of

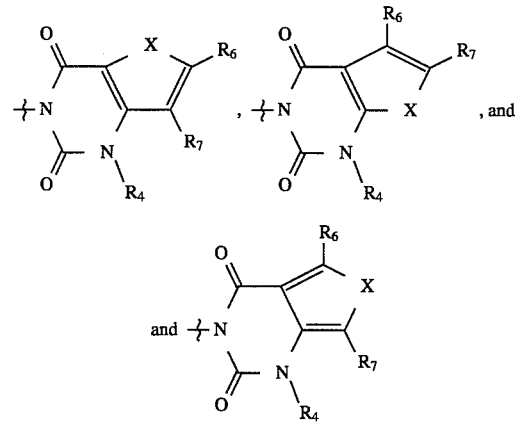

wherein X is selected from the group consisting of —N(R$_5$)—, —O— and —S— wherein R$_5$ is hydrogen or alkyl of one to six carbon atoms, and R$_6$ and R$_7$ are the same or different and are independently selected from the group consisting of hydrogen, alkyl of one to six carbon atoms, phenyl, halo, cyano, nitro, carboxy, alkoxycarbonyl of two to eight carbon atoms, and alkoxy of one to six carbon atoms.

5. A compound according to claim 1 wherein W is selected from the group consisting of

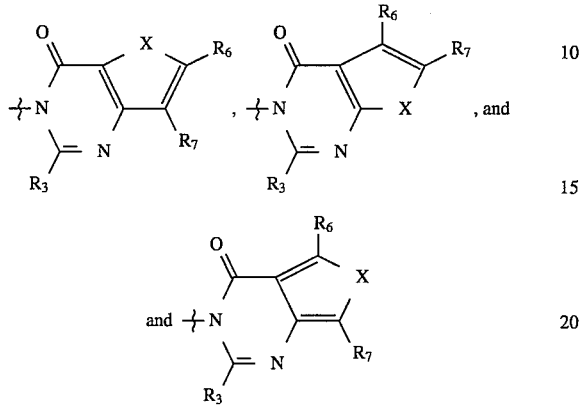

wherein X is selected from the group consisting of —N(R$_5$)—, —O— and —S— wherein R$_5$ is hydrogen or alkyl of one-to six carbon atoms, and R$_6$ and R$_7$ are the same or different and are independently selected from the group consisting of hydrogen, alkyl of one to six carbon atoms, phenyl, halo, cyano, nitro, carboxy, alkoxycarbonyl of two to eight carbon atoms, and alkoxy of one to six carbon atoms.

6. A compound according to claim 1 wherein W is selected from the group consisting of

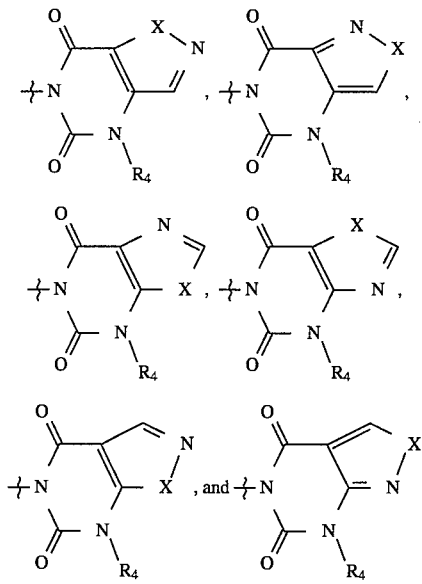

wherein X is selected from the group consisting of —N(R$_5$)—, —O— and —S— wherein R$_5$ is hydrogen or alkyl of one to six carbon atoms.

7. A compound according to claim 1 wherein W is selected from the group consisting of

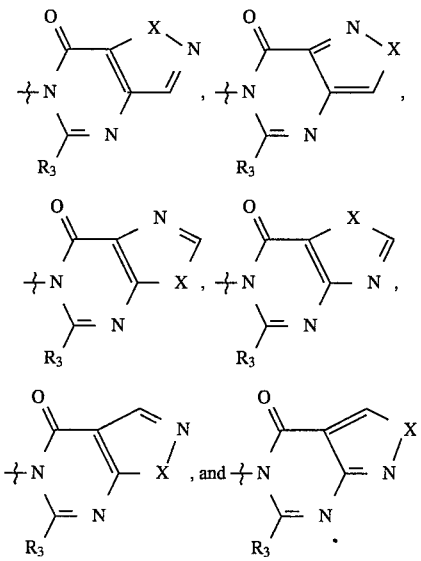

wherein X is selected from the group consisting of —N(R$_5$)—, —O— and —S— wherein R$_5$ is hydrogen or alkyl of one to six carbon atoms.

8. A compound according to claim 1 wherein W is

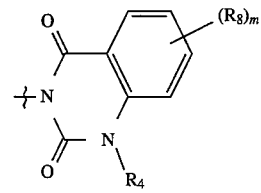

wherein m is selected from 1, 2 and 3 and, when m is 2 or 3, R$_8$ at each occurence is independently selected from the group consisting of hydrogen, alkyl of one to six carbon atoms, phenyl, halo, cyano, nitro, carboxy, alkoxycarbonyl of two to eight carbon atoms, alkoxy of one to six carbon atoms and, when m is 2, methylenedioxy and ethylenedioxy.

9. A compound according to claim 1 wherein W is

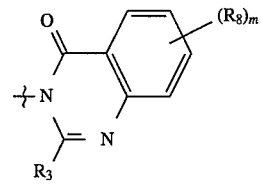

wherein m is selected from 1, 2 and 3 and, when m is 2 or 3, R$_8$ at each occurence is independently selected from the group consisting of hydrogen, alkyl of one to six carbon atoms, phenyl, halo, cyano, nitro, carboxy, alkoxycarbonyl of two to eight carbon atoms, alkoxy of one to six carbon atoms and, when m is 2, methylenedioxy and ethylenedioxy.

10. A compound according to claim 1 wherein W is selected from the group consisting of

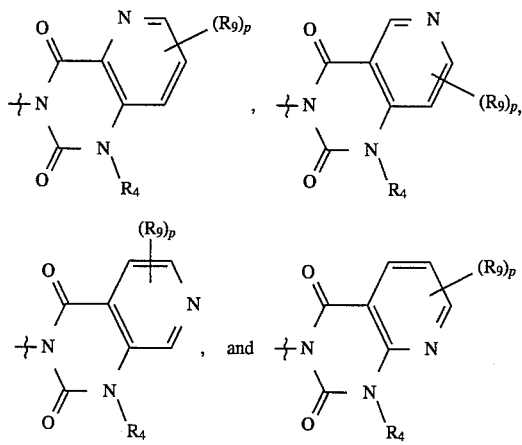

wherein p is selected from 1 and 2 and, when p is 2, R₉ at each occurence is independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

11. A compound according to claim 1 wherein W is selected from the group consisting of

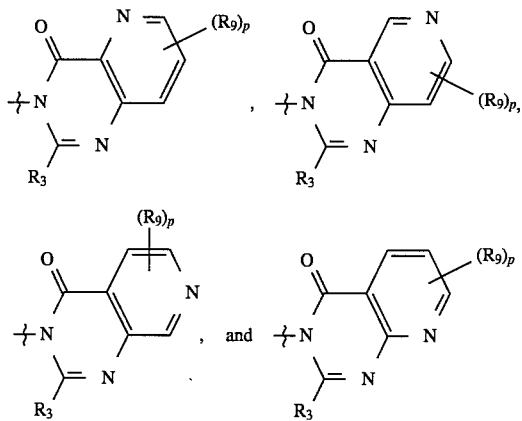

wherein p is 1 or 2 and, when p is 2, R₉ at each occurence is indpendently selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

12. A compound according to claim 1 wherein W is selected from the group consisting of

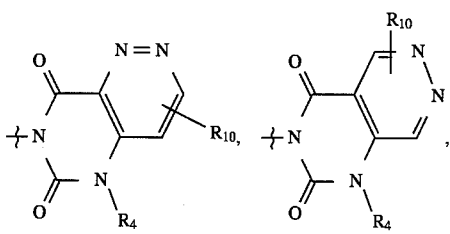

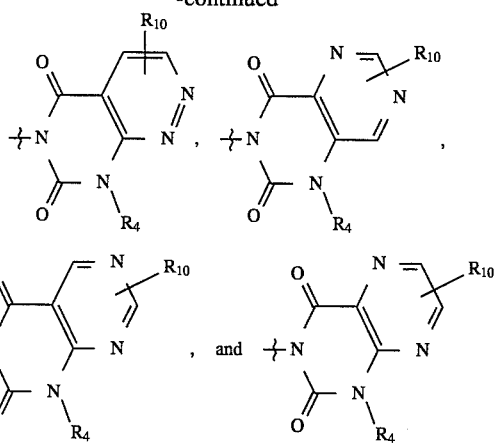

wherein $R_{10}$ is selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

13. A compound according to claim 1 wherein W is selected from the group consisting of

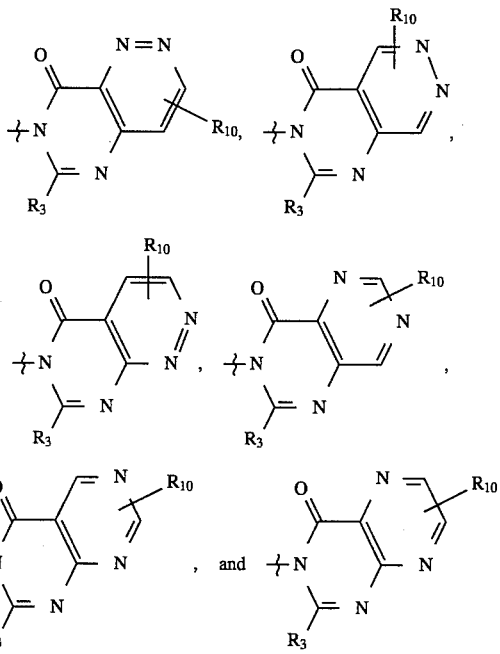

wherein $R_{10}$ is selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

14. A compound according to claim 1 wherein W is selected from the group consisting of

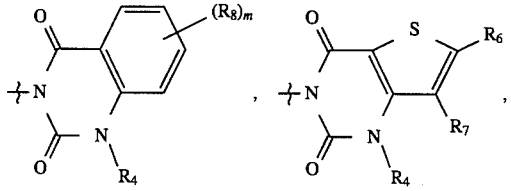

-continued

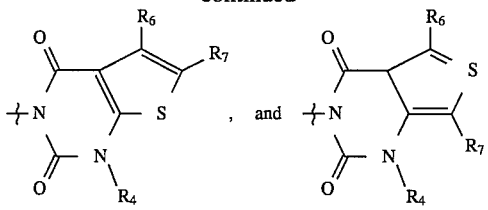

wherein m is selected from 1, 2 and 3 and, when m is 2 or 3, $R_8$ at each occurence is independently selected from the group consisting of hydrogen, alkyl of one to six carbon atoms, halo, cyano, nitro, carboxy, alkoxycarbonyl of two to eight carbon atoms and alkoxy of one to six carbon atoms and, when m is 2, methylenedioxy and ethylenedioxy, and $R_6$ and $R_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

15. A compound according to claim 1 wherein one of $R_1$ and $R_2$ is alkoxy of one to six carbon atoms and the other is hydrogen, n is selected from an integer from 2 to 4 and W is selected from the group consisting of

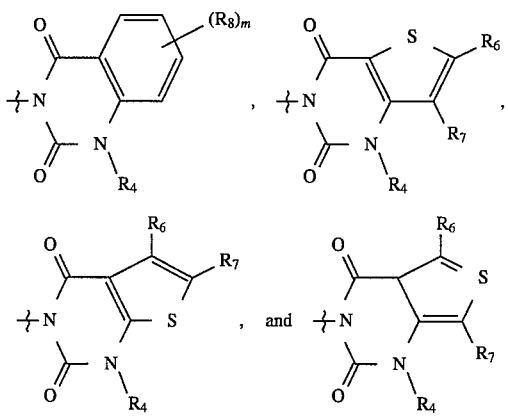

wherein m is selected from 1, 2 and 3 and, when m is 2 or 3, $R_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is 2, methylenedioxy and ethylenedioxy, and $R_6$ and $R_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms.

16. A compound according to claim 15 is selected from the group consisting of:

3-[2-(cis-6-Methoxy-2,3,3a,4,5,9b-hexahydro-[1H]-benz[e]isoindol-1-yl)ethyl]-8-methoxy-quinazoline-2,4(1H,3H)-dione;

3-[2-(cis-6-Methoxy-2,3,3a,4,5,9b-hexahydro-[1H]-benz[e]isoindol-1-yl)ethyl]-6,7-dimethoxy-quinazoline-2,4(1H,3H)-dione;

3-[2-(cis-6-Methoxy-2,3,3a,4,5,9b-hexahydro-[1H]-benz[e]isoindol-1-yl)ethyl]-7-chloro-quinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-thieno[2,3-d]pyrimidine-2,4(1H,3H)-dione;

3-[2-(cis-6-Methoxy-2,3,3a,4,5,9b-hexahydro-[1H]-benz[e]isoindol-1-yl)ethyl]-7-carbomethoxy-quinazoline-2,4(1H,3H)-dione;

3-[2-(cis-6-Methoxy-2,3,3a,4,5,9b-hexahydro-[1H]-benz[e]isoindol-1-yl)ethyl]-6-methoxy-quinazoline-2,4(1H,3H)-dione;

3-[2-(cis-6-Methoxy-2,3,3a,4,5,9b-hexahydro-[1H]-benz[e]isoindol-1-yl)ethyl]-6,8-dimethyl-quinazoline-2,4(1H,3H)-dione;

3-[2-(cis-6-Methoxy-2,3,3a,4,5,9b-hexahydro-[1H]-benz[e]isoindol-1-yl)ethyl]-1-methylquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-6,7-ethylenedioxyquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-6,7-dimethoxyquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-6,7-dimethoxy-quinazoline-4(1H,3H)-one; and 3-[2-(cis-6-Hydroxy-2,3,3a,4,5,9b-hexahydro-[1H]-benz[e]isoindol-1-yl)ethyl]-thieno[2,3-d]pyrimidine-4(1H,3H)-one;

or a pharmaceutically acceptable salt thereof.

17. A pharmaceutical composition comprising a therapeutically effective amount of a compound of claim 1 in combination with a pharmaceutically acceptable carrier.

18. A method of treating prostatism in a host mammal in need of such treatment comprising administering a therapeutically effective amount of a compound of claim 1.

19. A method of treating prostatism in a host mammal in need of such treatment comprising administering a therapeutically effective amount of a compound of claim 1 in combination with a 5-α reductase inhibitor.

20. The method of claim 19 wherein said 5-α reductase inhibitor is finasteride.

* * * * *